United States Patent [19]

Hoots et al.

[11] Patent Number: 5,389,548
[45] Date of Patent: Feb. 14, 1995

[54] MONITORING AND IN-SYSTEM CONCENTRATION CONTROL OF POLYELECTROLYTES USING FLUOROCHROMATIC DYES

[75] Inventors: John E. Hoots, St. Charles; Claudia C. Pierce, Naperville, both of Ill.; Roger W. Kugel, Winona, Minn.

[73] Assignee: Nalco Chemical Company, Naperville, Ill.

[21] Appl. No.: 219,126

[22] Filed: Mar. 29, 1994

[51] Int. Cl.6 .................................. G01N 21/64
[52] U.S. Cl. ........................... 436/6; 436/56; 436/85; 436/104; 436/120; 436/128; 436/129; 436/172
[58] Field of Search ............... 436/6, 56, 85, 104, 436/119, 120, 128, 129, 171, 172

[56] References Cited
U.S. PATENT DOCUMENTS 4,783,314 11/1988 Hoots et al. .
4,894,346 1/1990 Myers et al. .
4,992,380 2/1991 Moriarty et al. .
5,120,661 6/1992 Baker et al. .................. 436/164
5,128,419 7/1992 Fong et al. .

Primary Examiner—David A. Redding
Attorney, Agent, or Firm—Robert A. Miller; James J. Drake

[57] ABSTRACT

Concentration of a polyelectrolyte in the water of an aqueous system is controlled by first withdrawing a sample of the water and adding a known or standard amount of a fluorochromatic reagent to the sample. Then light energy is directed into the sample whereby light energy of a selected excitation wavelength for the fluorochromatic dye is available for absorption by the fluorochromatic reagent. The intensity of light emitted about a selected emission wavelength for the fluorochromatic reagent is measured and the intensity of the emitted light is compared to a standard curve, comprising a plot of fluorescence emission intensity of the fluorochromatic reagent in the presence of a polyelectrolyte versus concentration the polyelectrolyte. The concentration of the polyelectrolyte in the sample of water is determined from the comparison.

20 Claims, 3 Drawing Sheets

MONITORING AND IN-SYSTEM CONCENTRATION CONTROL OF POLYELECTROLYTES USING FLUOROCHROMATIC DYES

TECHNICAL FIELD OF THE INVENTION

The present invention is in the technical field of monitoring polyelectrolytes in aqueous systems, particularly monitoring polyelectrolyte concentration in industrial aqueous systems, and controlling the in-system concentration of polyelectrolyte-containing formulations.

BACKGROUND OF THE INVENTION

Polyelectrolytes, particularly water-soluble synthetic anionic, cationic and amphoteric polymers, are commonly added to aqueous systems as active components of water treatment formulations or for other purposes. The control goal of most water-treatment programs is to maintain a special ratio of water treatment agent(s) to target specie(s) (for instance scaling ions, corrodents, contaminants and the like) in the water of the system and/or to minimize or maintain specified system consumption of active treatment component(s). The feed and other treatment-agent concentration controls are regulated to attain or maintain that ratio or specified treatment target dosage. The concentration fluctuations of a water treatment agent in an industrial aqueous system can defy conventional control means, preventing the target ratio or specified dosage from being uniformly maintained. Polyelectrolytes and other treatment agents may be lost to the aqueous system due to system consumption (selective losses such as treatment-activity consumption, deposit, corrosion, chemical and microbiological degradation processes and the like), hydraulic losses or removal (nonselective losses such as blowdown, drift and the like) and combinations of such phenomena. Treatment agents are replenished by feed of fresh formulation, but a precise replenishment requires a quantification of current in-system concentration.

Quantification of the in-system concentration of a treatment agent by quantification of all individual losses of the agent from the system may be an unreachable objective for most industrial systems. The extent of all such losses, and even the sources of all such losses, are seldom exactly known. Determination of the concentration of an active treatment component by conventional analysis techniques are often unsatisfactory. Such techniques commonly are not as beneficial as desired because of one or more of the following problems: background interferences from the system liquid or materials contained therein; bulky and/or costly equipment requirements; and inaccurate readings due to failures to detect one or more types of loss from the system, such as degradation or deposition within the system long delay time between when (manual) analyses are conducted and response (e.g., change in chemical feed rate) is initiated.

The target concentration of a polyelectrolyte and other active treatment components in the system may also elude system operators because of other operational abnormalities. Monitoring not only the current in-system concentration of a treatment agent but also its selective loss from the system would provide an indicator of treatment program performance.

If an in-system concentration of a polyelectrolyte and its selective loss from the system can be monitored, particularly if such monitoring permits both the concentration and the extent of loss to be quantified and if the monitoring is continuous, automatic control can permit polyelectrolyte-loss compensation, and a precise control over the in-system concentration and system consumption. If the extent of polyelectrolytes loss is instead only an inaccurate estimate, or if the monitoring for any reason fails to provide expeditious and reliable data on the concentration of a polyelectrolyte in an aqueous system, the responsive feed adjustment may result in a severe and deleterious underfeeding or a wasteful, and deleterious overfeeding of the treatment formulation. When for instance a polyelectrolyte is being added to an aqueous system to inhibit deposit formation and/or corrosion therein, a responsive feed adjustment that underfeeds the polyelectrolyte may be followed by deposit formation and/or corrosion within the system.

U.S. Pat. No. 4,783,314, John E. Hoots and Barry E. Hunt, issued Nov. 8, 1988, incorporated hereinto by reference, provides a method for monitoring a water treatment component by incorporating at least one fluorescent compound as a tracer into the treatment formulation to provide quantitative measurement/control of the treatment feed rate and performance. The concentration of a given fluorescent tracer in the aqueous system at a given point in time is generally determined by comparing the fluorescence emissivity of a sample from the system to a standard or a standard curve of fluorescent tracer concentration versus emissivity. Suitable fluorescent tracers for this method are substantially both water soluble and inert in the environment of the aqueous system in which they are used. This method at times herein is referred to as the "inert tracer" method.

U.S. Pat. No. 4,992,380, Barbara E. Moriarty, James J. Hickey, Wayne H. Hoy, John E. Hoots, and Donald A. Johnson, issued Feb. 12, 1992, incorporated hereinto by reference, describes a method for continuously monitoring a treating agent added to a body of water employed in a cooling tower by the characteristics of an inert tracer proportioned to the treating agent.

U.S. Pat. No. 5,128,419, Dodd W. Fong and John E. Hoots, issued July 7, 1992, incorporated hereinto by reference, describes a post-polymerization derivatization method for preparing polymers having pendant fluorescent groups. Polymers so marked or tagged may be monitored by fluorescence spectroscopy to determine the location, route, concentration at a given site and/or some property (for instance leachability) of these polymers and/or a substance in association with these polymers. As discussed therein, conventional techniques for monitoring polymers are generally time consuming and labor intensive, and often require the use of bulky and/or costly equipment. Most conventional polymer analysis techniques require the preparation of calibration curves for each type of polymer employed, which is particularly time consuming and laborious when a large variety of polymer chemistries are being employed. Conventional analysis techniques that determine analytically the concentration of a polymer's functional groups are generally not practical for industrial use, particularly when it is desired to monitor a polymer on a frequent or continuous basis, or when rapid results are needed. Indirect analysis techniques may provide results faster using simpler techniques, but in many instances even faster and/or more accurate determinations are highly desirable. If the fluorescent group incorporated into a polymer is derived from a highly fluorescent molecules, its presence will permit the monitoring of the polymer at concentration levels down to 0.1 ppm or less, even when the polymer is tagged with only one part by weight of the fluorescent group per 100 parts by weight of polymer. The post-polymerization is a (trans)amidation derivatization of preexisting polymers having carbonyl-type pendant groups, including pendant carboxylic acid, carboxylic acid ester and amide groups. This post-polymerization derivatization method is exemplified in U.S. Pat. No. 5,128,419 using a variety of starting-material polymers, including acrylic acid homopolymers, acrylic acid/acrylamide copolymers, acrylic acid/acrylamide terpolymers with sulfomethylacrylamide, vinyl acetate, acrylonitrile and methacrylic acid. At times herein the terminology of "tagged polymers" are used to refer to these polymers and/or other pendant-fluorescent-group-containing polymers prepared by other methods.

Prior to the above-mentioned inventions that utilize fluorescence spectroscopy or other methods to provide to the water treatment field simple, accurate and rapid monitoring techniques, the fastest technique for on-site monitoring of polymeric treatment components was the "PA-1/PA-2" polyacrylate turbidity test. This turbidity test technique determines the concentration of polymers having pendant carboxylic acid groups based on a reaction between the carboxylic acid groups and a cationic organic compound. The reaction product forms as a suspension of insoluble colloidal particles and the measure of polymer concentration is the reaction mixture turbidity. At times herein this PA-1/PA-2 polyacrylate turbidity test is referred to as merely "the turbidity test".

The turbidity test and fluorescence analysis of tagged polymers are both analytical techniques that are directed to the polymer itself rather than on an associated inert tracer. The turbidity test is, however, limited in selectivity and thus prone to interferences from substances other than the polymer in question. For instance, nonpolymeric surfactants and other organics can also produce turbidity under test conditions, and color and/or turbidity might be present in the water sample as obtained. The turbidity forming reaction can be interfered with by inorganic ions or other sources of turbidity in the water. The turbidity test is also limited in its industrial application by the time and/or technique dependence of its results (result variations occurring with the operator's technique or the length of time before the turbidity reading).

The monitoring of fluorescent tagged-polymers is of course limited to polymers that have been provided with pendant fluorescent groups that endure under the conditions of the aqueous system. A given polymer may not be commercially available in tagged form, or may not be readily tagged.

A method for determining the concentration of polysulfonate and/or polycarboxylate compounds in a solution sample by adding a metachromatic dye thereto and then comparing the solution's absorbance to that of standard solutions is described in U.S. Pat. No. 4,894,346, Myers et al., issued Jan. 16, 1990. Metachromasy is the color-changing phenomenon of certain dyes upon interaction or complexation with a polyelectrolyte. The color of dyes is derived from their ability to absorb light in the visible region of the spectrum, between about 400 and 800 nm. Absorption is caused by electronic transitions in the molecules and can occur in the visible region only when the electrons are reasonably mobile. Mobility is encouraged by unsaturation and resonance. The main structural unit of a dye, which is always unsaturated, is called the chromophore, and a compound containing a chromophore is called a chromogen. Auxochromes, such as hydroxyl, amino and carboxyl groups, are substituent atoms or groups that effect the intensity and at times the absorption band of a chromophore. The hue, strength and brightness of a dye depend on the entire light-absorbing system of the dye molecule. In general, for a given type of dye, extension of the unsaturated system, which increases the opportunities for resonance, shifts the absorption of light toward longer wavelengths. Then the color that is absorbed progresses across the visible spectrum from violet to purple, and the color seen by the human eye is the color complementary to that absorbed. A metachromatic color-change is seen when an ionic dye interacts with an oppositely-charged polyelectrolyte in solution. The interaction or complexation that produces the color change is believed to result from the aggregation of dye molecules as a consequence of three types of forces, i.e., the electrostatic attraction between an ionic dye and oppositely-charged sites on the polyelectrolyte, the hydrophobic attraction of dye molecules to nonpolar regions of a polyelectrolyte, and the pi-electron interaction between adjacent or closely proximate dye molecules. The color change results from a shift in a dye's maximum absorbance wavelength (absorptive metachromatic shift).

Some metachromatic dyes are fluorescent. It has been observed that the fluorescence intensity of certain polycyclic aromatic reagents increased when they interacted with various cationic or nonionic polymers, and a secondary method utilizes this phenomenon and the affinity of the resulting complexes to biological polyanions to form ternary complexes for use in fluorescence microscopy, flow cytometry and other quantitative method, as described in European Patent No. 0 231 127, A. L. Wu, 1987.

Another quantitative method employs the complexing interaction between an anionic reagent and a cationic polyelectrolyte (but not the metachromatic spectral change, if any), whereby a complex that can be extracted with a hydrophobic solvent is formed, as is described in Anal. Chem., D. P. Parazak, C. W. Burkhardt and K. J. McCarthy, Vol. 59, pages 1444–1445, 1987.

Monitoring a polymeric treatment agent using both an associated inert tracer and a quantitative analytical technique permits the determination of the system consumption for the polymer and indicates the severity of the operating conditions. It also permits-a "performance based" polymeric-treatment in-system concentration control method. The polymer feed or other polymer-concentration control is correlated to selective system consumption for the polymer and compensates also for nonselective polymer removal by hydraulic losses (removal with blowdown, drift and the like) and any operational abnormalities (changes in pumping rates of chemical feed pump and the like). Such dual monitoring would permit differentiation between selective and nonselective polymer losses. As the severity of operating conditions increases/decreases (system consumption), the target polymer concentration can be concomitantly increased/decreased. Such monitoring and in-system concentration control methods are of course restricted by the requirements of, and limitations inherent in, the quantitative analytical technique chosen.

It is an object of the present invention to provide a method for monitoring and/or controlling polyelectrolyte losses and/or dosages in an aqueous system, particularly on a continuous basis. It is an object of the present invention to provide a method for monitoring and/or controlling polyelectrolyte concentrations in an aqueous system that is substantially independent of an operator's laboratory technique. It is an object of the present invention to provide a method for monitoring and/or controlling polyelectrolyte concentrations in an aqueous system that provides a response that is substantially linear to polyelectrolyte concentration. It is an object of the present invention to provide a method for determining the system consumption for a polyelectrolyte that includes a selective quantitative analytical technique that is not limited to tagged or other specialty polymers. It is an object of the present invention to provide a polyelectrolyte "system consumption" in-system concentration control method that includes a selective quantitative analytical technique that is not limited to tagged or other specialty polymers. These and other objects of the present invention are described in more detail below.

DISCLOSURE OF THE INVENTION

The present invention provides a method for monitoring and/or controlling polyelectrolyte concentration in aqueous systems, particularly industrial aqueous systems, that at least includes a determination of the change in a fluorescence characteristic of a certain type of reagent when one of such reagents are introduced into a sample taken from the aqueous system. The present invention provides a method for determining the system consumption for a polyelectrolyte that combines a determination of the change in fluorescence intensity of a certain type of reagent when one of such reagents are introduced into a sample of the aqueous system together one or more inert tracer(s) determinations. The present invention provides a polyelectrolyte in-system concentration control method that includes a determination of the change in fluorescence intensity of a certain type of reagent when one of such reagents is introduced into a sample taken from the aqueous system and a monitoring of the concentration of at least one inert tracer associated with the polyelectrolyte. The type of reagents employed in the present invention are at times herein referred to as "fluorochromatic reagents", as will be described in more detail below.

PREFERRED EMBODIMENTS OF THE INVENTION

Figure 1:
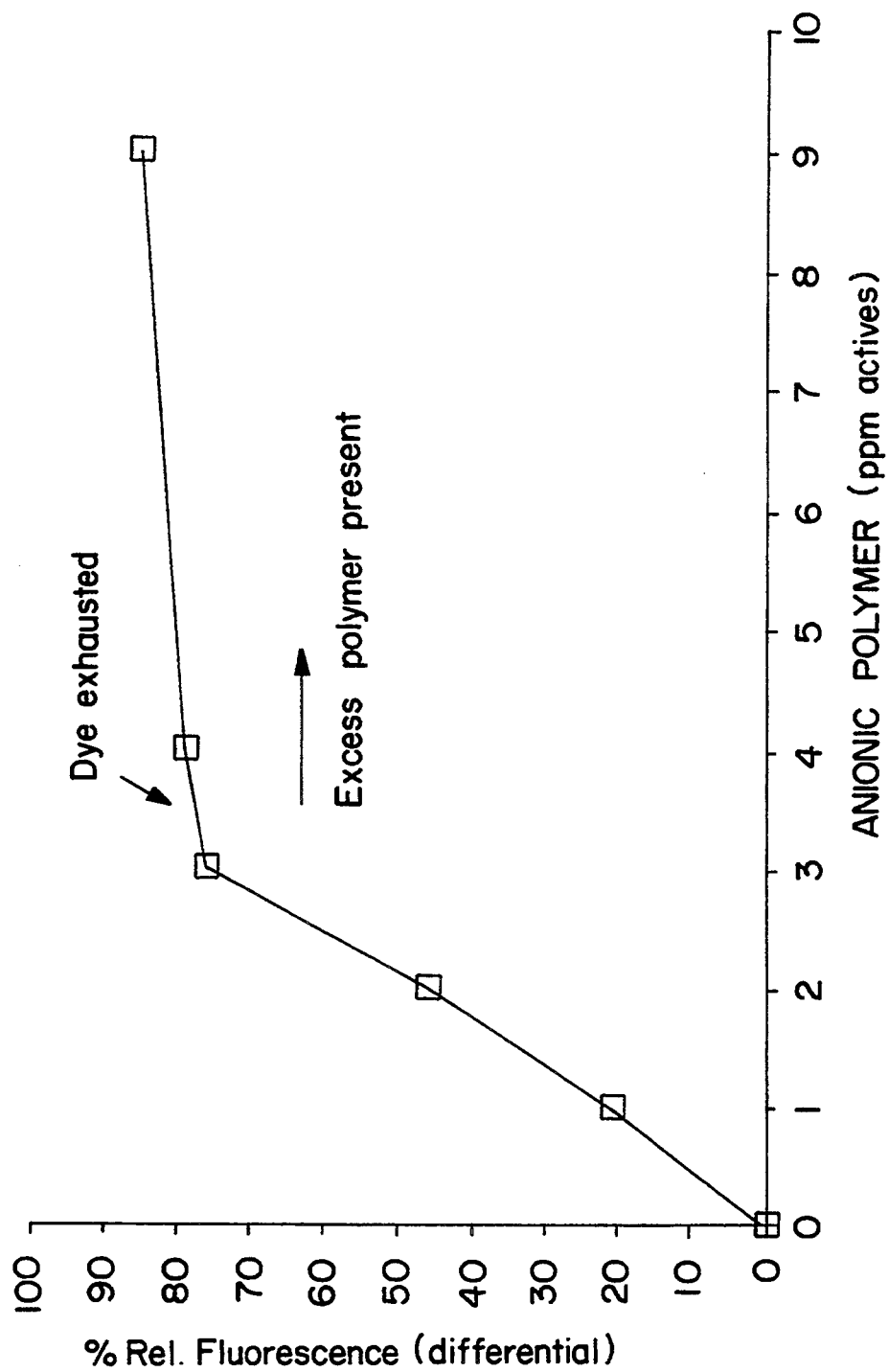
FIG. 1 is a set of two plots of percent relative fluorescence versus emission wavelength for an aqueous solution of fluorochromatic reagent in the absence of polyelectrolyte and for an aqueous solution of fluorochromatic reagent in the presence of polyelectrolyte.

The present invention employs fluorochromatic reagents. A fluorochromatic reagent is fluorescent, or potentially fluorescent, or a reagent whose fluorescence properties change in the presence of a polyelectrolyte. It is a compound that absorbs light of a given wavelength and emits it, or fluoresces, at a longer wavelength and/or with increased/decreased fluorescence intensity before and/or after the fluorochromatic interaction has occurred. The main structural unit of a fluorescent or potentially fluorescent reagent, which is always unsaturated, is called the fluorophore. Fluorochromatic reagents are ionic, fluorescent or potentially fluorescent reagents that interact with oppositely charged polyelectrolytes whereby there is a change in their fluorescence characteristics. When the fluorochromatic reagent is fluorescent before the fluorochromatic interaction, the intensity of its fluorescent emission at its normal peak emission wavelength is changed. It has been found that, in a reasonably dilute aqueous solution containing a polyelectrolyte, a fluorochromatic reagent will exhibit at least one of several types of polyelectrolyte-concentration-dependent behaviors. These behavior types can be classified by the behavioral effect seen when polyelectrolyte concentration is increased, as follows:

(A) less intense emission when measured about a normal emission wavelength peak;
(B) more intense emission when measured about a normal emission wavelength peak; and
(C) the appearance of a new emission peak and/or a more intense emission when measured about the new emission wavelength peak (and concurrent change in the excitation wavelength may also occur).

Since the extent of the behavior seen is dependent upon the concentration of the polyelectrolyte, it can be used to determine the concentration of the polyelectrolyte as described in more detail below.

The type of behavior shown is dependent upon the chemical structure of the fluorochromatic reagent and/or the polyelectrolyte/fluorochromatic reagent ratio. A fluorochromatic fluorescence change is seen when the ionic fluorochromatic dye interacts with an oppositely-charged polyelectrolyte in solution. The interaction or complexation that produces the fluorescence change is believed to result from the aggregation of reagent molecules as a consequence of three types of forces, i.e., the electrostatic attraction between an ionic fluorochromatic reagent and oppositely-charged sites on the polyelectrolyte, the hydrophobic attraction of the reagent molecules to nonpolar regions of a polyelectrolyte, and the pi-electron interaction between adjacent or closely proximate dye molecules. The decrease in the intensity of the fluorescence emissions at a normally peak emission wavelength (Type A behavior) as seen in some fluorochromatic reagents has been found to be an emission quenching phenomenon, and such phenomenon can be considered a fluorochromatic quenching. The change (increase, decrease, and/or appearance) of the fluorescence emissions as seen in other fluorochromatic reagents has been found to be fluorescent emission (and/or excitation) wavelength appearance and/or shift phenomenon (Type C behavior). In a non-fluorescent reagent, a new fluorescent emission may appear upon interaction with the polyelectrolyte. In a fluorescent reagent, a new fluorescent emission may appear with or without a change in existing fluorescent emission. A fluorochromatic dye exhibiting an emission wavelength shift phenomenon decrease in pre-existing fluorescent emission, appearance of a new fluorescent emission and/or change (appearance) in excitation wavelength in the presence of a polyelectrolyte is exhibiting a combination of Type A and Type B behavior, and either can be used to determine the concentration of the polyelectrolyte. Type C behavior includes such emission wavelength shifting phenomenon and may also include the appearance of fluorescence (the new emission wavelength peak) in a previously weak or nonfluorescent compound.

Fluorochromatic reagents include, but are not limited to, Nile Blue A and pinacyanol chloride.

In preferred embodiment, the process of the present invention includes the tracing or tracking of the polyelectrolyte in the water system in combination with one or more inert tracers. An inert tracer is a chemical specie that is substantially undepleted by the water system's environment, as is described in detail below. Since the polyelectrolyte may be consumed to some extent between its addition to the water system and the sampling, and an inert tracer is substantially unconsumed, an associated inert tracer determination is a measure of the zero-consumption concentration of the polyelectrolyte, that is the polyelectrolyte concentration that would exist if no significant polyelectrolyte system consumption had occurred. The determination of the actual polyelectrolyte concentration (or, when more convenient, the polyelectrolyte concentration in terms of product) is made using the fluorochromatic reagent. The difference between these two measurements is the level of polyelectrolyte consumption or selective polyelectrolyte loss (system consumption).

The feed of polyelectrolyte water treatment agents to a water system, particularly an industrial water system, seldom is on a one-time slug basis. Such water systems are seldom static, and instead water is being added to, and lost from, the system. After an initial addition or feed of a water treatment agent to a system, a maintenance feed of the agent is routinely continued. The maintenance feed can be added on an intermittent, semicontinuous or substantially continuous basis, depending on the rate of exchange of water and/or other dynamic features of the water system.

The fluorochromatic measurement of the actual concentration of polyelectrolyte at the sampling site alone is of value. It can assure that transport of the active treating agent to the sampling site has in fact occurred. It can also determine an underfeeding or overfeeding of the active treating agent, and alone provide a signal that can activate or regulate the maintenance feed of the active treating agent.

The target concentration of an active treatment agent at any given site is preferably chosen by considering the system consumption upon the active treating agent. System consumption is dependent upon many parameters which may fluctuate over time in a given system or vary from one system to another. Reasonably accurate estimations of such system consumption of treating agent factors can be difficult. The combined use of the fluorochromatic determination of the actual polyelectrolyte in-system concentration and the determination of in-system concentration of an associated inert tracer will not only provide the system consumption of a treating agent for the specific system at the given time, but also permit accurate target polyelectrolyte concentrations to be set or the minimization of the system demand to be attained.

The fluorochromatic determination of actual polyelectrolyte concentration at a given site in a water system is preferably comprised of withdrawing a sample of the water at such site, adding a known or standard amount of a fluorochromatic reagent to the sample, directing energy in the form of light into the sample so that the energy of a specific wavelength (the selected excitation wavelength for the fluorochromatic reagent) is available for absorption by the fluorochromatic reagent, measuring the intensity of the fluorescent light emitted about a specific, and longer, wavelength (the selected emission wavelength for the fluorochromatic reagent), and then comparing the intensity of the emitted light to a standard curve. The standard curve preferably is a plot of intensity of the emitted light versus the polyelectrolyte concentration, the amount of the fluorochromatic reagent and the excitation/emission wavelengths being standard. The standard curve may also contain a correction for background fluorescence (although this factor is typically small), as is described later.

The standard curve may be specific for the given polyelectrolyte, or instead it may be calibrated on the basis of polyelectrolyte ionic sites, which are then converted to polyelectrolyte concentration based on the charge density of the given polyelectrolyte. As illustrated in the Examples hereof which are described below, this determination is dependent upon an interaction between fluorochromatic reagent and polyelectrolyte ionic sites, which interaction, for example, decreases the fluorescent intensity at the selected emission wavelength (which is Type A behavior). When this mole ratio limit is exceeded, the fluorochromatic reagent available for interacting with the ionic sites can be considered exhausted. The slope of the plot of emission intensity versus polyelectrolyte concentration levels off when this ratio limitation is met, and the standard curve no longer provides the desired correlation between fluorescent emission intensity and polyelectrolyte concentration. The ionic site to fluorochromatic reagent mole ratio limitation can be determined empirically for any desired combination of polyelectrolyte and fluorochromatic reagent, or it can be estimated based on a known or estimated charge density of the polyelectrolyte. A prudent estimate of the ionic site to fluorochromatic reagent mole ratio limit may presume that the limit will fall above a 1:1 mole ratio and set the limitation at the estimated 1:1 mole ratio to assure the limitation is not exceeded, although it is believed that for most Type A behavior polyelectrolyte/fluorochromatic reagent combinations the actual limit will be found within the range of from about 1.2:1 to about 1.5:1 mole ratio of polyelectrolyte ionic sites to fluorochromatic reagent.

The amount of fluorochromatic reagent added to the sample preferably should be selected to avoid the ionic site to fluorochromatic reagent mole ratio limitation, based on the probable polyelectrolyte concentration range to be encountered at a given site. If desired, a polyelectrolyte concentration determination can be easily confirmed by this method, using another sample, and more fluorochromatic reagent. If the actual change in fluorescence is unchanged when first and second samples are compared, then the ionic site to fluorochromatic reagent mole ratio limitation has not been reached. Higher concentrations of polyelectrolyte can be measured by increasing the concentration of the fluorochromatic reagent.

As noted above, the decrease in emission intensity at the selected wavelength, which preferably should be at or about an emissions peak for the given fluorochromatic reagent in the absence of polyelectrolyte, may be due to a fluorochromatic quenching or a fluorochromatic wavelength shift, and the possibility of both phenomena occurring in some fluorochromatic reagents cannot be excluded. Which phenomenon is occurring is believed dependent on the fluorochromatic reagent selected. Most advantages of the present invention can be realized regardless of which phenomenon is occurring. Nonetheless, in preferred embodiment the fluorochromatic reagent employed is one that provides a decrease and/or increase in fluorescent emission intensity at the selected wavelength due to fluorochromatic wavelength shift or appearance (within Type C behavior).

More details concerning fluorescence analysis, including selection of excitation/emission wavelengths, diminishing background interferences, and the like are described below in general and for the inert tracer, and such techniques are applicable to the fluorochromatic determination where appropriate.

When the fluorochromatic determination is combined with an inert tracer determination, the system consumption for the polyelectrolyte between the addition and sampling sites, or between an upstream and downstream sampling sites, can be determined from the following Formula:

$$C_1 - C_2 = SC$$

wherein $C_1$ is the polyelectrolyte concentration added to the system, or a factor proportional to polyelectrolyte concentration added to the system, as determined by the inert tracer method, $C_2$ is the polyelectrolyte concentration, or a factor proportional to polyelectrolyte concentration, as determined by the fluorochromatic method, and SC is the system consumption (the amount of polyelectrolyte selectively consumed by the system rather than lost by some other mechanism, such as hydraulic losses), in terms of amount of polyelectrolyte consumed per unit volume of the water of the water system.

The present method does not exclude the use of any of the information provided thereby for other purposes, including but not limited to the monitoring of hydraulic characteristics of the water system, including but not limited to throughput times, water stream routes, mixtures of multiple streams, channeling, rise rate, carry over, cross contamination, leaks between systems, flow paths and rates, and the like where desired, by a comparison between such information and a known relationship between the presence and/or concentration of the polyelectrolyte and/or inert tracer and such hydraulic characteristic.

In those circumstances where the creation or destruction of polyelectrolyte ionic sites in situ within a system, for instance by hydrolysis of acrylamide mer units, occurs, the concentration of the polyelectrolyte determined by the fluorochromatic determination is in terms of ionic site equivalents to the polyelectrolyte as initially introduced into the water system. For example, destruction of polyelectrolyte sites due to chemical degradation or other mechanism would be detected as system consumption of the polyelectrolyte.

According to one embodiment of the invention, the polyelectrolyte in-system concentration can be adjusted by the invention to provide a substantially optimal in-system concentration based on optimization of the results obtained where $C_1 - C_2$ (i.e. SC) is minimized. A system-consumption-minimized value for polyelectrolyte treatment in-system concentration may be used to provide a signal that regulates the polyelectrolyte feed to the water system accordingly. The other losses of the polyelectrolyte to the water system and changes in the concentration of the polyelectrolyte in the water system may also be taken into account in the value of $C_1$ above.

The disadvantageous time delay between sampling and completion of the analysis that is attendant on many conventional analytical techniques for polyelectrolytes is avoided by the present invention. The time required for sampling and addition of the fluorochromatic reagent is negligible, and can readily be done on a continuous basis. The time required for the development of the fluorochromatic effect in some cases from about instantaneous to about one or two minutes. In other cases the development of the fluorochromatic effect may take 30 minutes, or an hour or more. The excitation of the sample and the reading of the emission intensity can readily be conducted on-site, in the manner described elsewhere herein.

Also avoided in some preferred embodiments of the invention are the problems that occur when visible dyes are added to the entire water system. Visible dyes, or dyes, or such terminology as used herein, and as understood generally in the chemical field, are colored substances that bring about a significant degree of coloration in other materials when dispersed therein, which coloration characteristic is due to their strong absorption of electromagnetic radiation in the visible region, which extends from about 4000 to about 7000 Angstroms, or from about 400 to about 700 nm. The primary advantage in using visible dyes is to permit analysis by sight. The color imparted to the water system by visible dyes is nonetheless often a major disadvantage regardless of whether the water system is a cooling water system, a boiler water system, a waste water system or the like. The color gives the water system a tainted appearance. The color normally persists, and taints the appearance of effluents and/or recycled fractions. The persistent color can even at times diminish the recycling potential of a water treatment process.

When a visible dye is added to an entire water system, there of course will be a time delay between its addition and the taking of a water sample for analysis, during which the dye may be susceptible to degradation by chlorine present in the water system and/or air oxidation. A large amount of a visible dye must be used when it is added to an entire water system in comparison to the minute amount of chemical required to analyze a small side-stream water sample by the process of the present invention when the fluorochromatic reagent is added only to the sidestream sample. When the concentration of a visible dye is determined by light absorbance measurements, such measurements will typically be about three to four orders of magnitude (100–1,000 times) less sensitive than fluorescence measurements. Moreover, the concentration of visible dyes required for their monitoring purposes can add to the organic loading of the water system and thus be a detrimental factor to the water treatment process.

In preferred embodiments of the present invention, an inert tracer is used which is not a visible dye. In preferred embodiments of the present invention, the fluorochromatic reagent is not added to the water system, but only to a sample taken therefrom, and if added to the water system itself, the in-system concentration thereof is not sufficient to visibly affect the appearance of the water of the system or significantly add to its organic loading, as described below.

Unlike an inert tracer which must be added to the system together with, or in close proximity to, the polyelectrolyte, and which must be added in proportion to the polyelectrolyte, the fluorochromatic reagent preferably is added only to a sample taken from the water system. The fluorochromatic reagent is being used for determining the presence and/or concentration of the polyelectrolyte at a given site, which determination is made possible by the interaction of the polyelectrolyte and the fluorochromatic reagent. This preferred embodiment not only avoids the coloration, and organic loading, of the water system to any extent by the fluorochromatic reagent, but also avoids the consumption of ionic sites on the polyelectrolyte in the water system by the polyelectrolyte/fluorochromatic dye interaction. Since the polyelectrolyte being monitored is an active treatment agent, in most, but not necessarily all, circumstances the ionic sites of the polyelectrolyte are related to its treatment activity, and thus consumption of such sites could have deleterious effects.

The present invention in broad embodiment does not, however, exclude a process wherein the fluorochromatic reagent is added to the entire water system or portion thereof that is more extensive than a small side-stream sample. The time delay between its addition and the taking of a water sample for analysis may expose the fluorochromatic reagent to degradation by chlorine present in the water system and/or air oxidation. A significantly larger amount of the fluorochromatic reagent must be used than the amount required to analyze a small side-stream water sample. The larger amounts of fluorochromatic reagents required when added to the entire water system may add to the organic loading of the water system and thus be a detrimental factor to the water treatment process. Nonetheless such embodiment of the present invention would retain at least the advantage of the greater sensitivity of fluorescence measurements in comparison to the determination of the concentration of a visible dye by light absorbance measurements, which are typically about three to four orders of magnitude less sensitive than fluorescence measurements.

As mentioned elsewhere herein, the present invention in preferred embodiments includes the use of a fluorochromatic reagent in combination with an inert tracer. As described in U.S. Pat. No. 4,992,380, the decision of which is incorporated hereinto by reference, inert tracers can be employed for continuous on-stream monitoring of a treatment agent added to a circulating body of water. Such a circulating body of water may be that in a cooling tower, boiler system, waste water treatment plant or the like which may have unknown sources of water gains or losses effecting the concentration of the treatment agent. In such circumstances, even apparently sophisticated feed control equipment based on flow rate, for instance based on blowdown or carefully metered chemical feed, cannot assure that the target treatment agent concentration in the water system is being met. The chemical treatment of industrial cooling water, boiler water and other waters to prevent or diminish corrosion, scaling, and other encroachments has become very complex and concomitantly there has arisen a great need to determine treatment agent concentration by the testing of the water to which the agent is added. The new treatment programs are to a great extent based on environmentally-safer polyelectrolytes that both require tight control for optimum performance and are difficult to test, for instance by light absorbance methods, for in industrial water. The concentration of a treatment-active polyelectrolytes will change upon polyelectrolyte loss due to treatment-activity consumption, deposit, and chemical and microbiological degradation processes, such processes are referred to as system consumption. Tracking such polyelectrolyte-selective concentration changes is of course best accomplished by the direct monitoring of the polyelectrolyte. Other polyelectrolyte concentration variations are due to physical losses and the addition and loss of water from the system, which are due to measured blowdown, unaccounted blowdown, drift, leakage, overflow, incorrect maintenance feed rates, evaporation, unregulated additions of makeup water, unregulated diversion of system water for other purposes and the like and combinations of such phenomena. Such concentration variations are not selective to a polyelectrolyte treatment agent and will have a substantially like effect on an inert tracer that is added to the system together with the polyelectrolyte. When an inert tracer that is readily monitored, particularly as to its concentration; is added to the system in known proportion to a polyelectrolyte treatment agent, the nonselective concentration variations of the polyelectrolyte can be readily determined. The other causes of concentration changes of the inert tracer, referred to as nonselective consumption, will be proportional to those of the polyelectrolyte.

To be most useful in a determination of nonselective polyelectrolyte consumption, an inert tracer preferably is transportable in the water system to the same degree as the polyelectrolyte and preferably also meet the following criteria:

1. Be detectable on a continuous or semicontinuous basis and susceptible to concentration measurements that are accurate, repeatable and capable of being performed on many different types of waters, such as clean water, turbid water, hard or soft waters, and the like;
2. Be substantially foreign to the chemical compounds that are normally present in the water systems in which the inert tracer may be used;
3. Be substantially impervious to interference from, or biasing by, the chemical compounds that are normally present in the water systems in which the inert tracer may be used;
4. Be substantially impervious to any of its own potential selective losses to the water system;
5. Be compatible with all treatment agents employed in the water systems in which the inert tracer may be used, and thus in no way reduce the efficacy thereof;
6. Be compatible with all components of its formulation, which is preferably a formulated product that also contains the polyelectrolyte which will be monitored, despite the required concentrations of the tracer and/or other components and despite the storage and/or transportation conditions encountered; and 7. Be reasonably nontoxic and environmentally safe, not only within the environs of the water system in which it may be used, but also upon discharge therefrom.

Generally, it is desirable to employ the least amount of inert tracer that is practical for the circumstance, and the amount of the inert tracer added to the water system should be at least an amount sufficient for the determinations desired. Seldom would an inert tracer be deliberately fed to a water system in an amount grossly in excess of the minimum effective amount because there generally would be no practical purpose in doing so that would justify the costs involved. The amount of inert tracer to be added to the inert tracer-receiving water system that is effective without being grossly excessive will vary with a wide variety of factors, including without limitation the inert tracer and monitoring method selected, the potential for background interference with the selected monitoring method, the magnitude of the expected inert tracer concentration at the sampling site(s), the monitoring mode (on-line continuous, semi-continuous, slug-and-sample, and the like), and other similar factors. Generally, the in-system concentration of an inert tracer added to a water system will be at least sufficient to provide a concentration of tracer in the water system of at least about 0.1 ppb, and more commonly at least about 10 ppb or higher, such as at least about 10 ppm, at the sampling site(s).

By the terms "tracing" and "tracking" is meant herein, unless expressly indicated otherwise, the determination of at least the presence of the inert tracer(s) in at least one sample of the water system, and preferably the concentration of the inert tracer(s) in such sample. Such tracing can be conducted on a singular, intermittent, semi-continuous or continuous basis, and preferably is conducted on-site, at the site of the water system, and preferably on a continuous basis.

As noted above, the inert tracer is added to the water system in known proportion to the polyelectrolyte being tracked. The preferred method of achieving such proportionate addition is to formulate the inert tracer together with the polyelectrolyte. The formulation, or "product", may be an aqueous solution or other substantially homogeneous admixture that disperses with reasonable rapidity in the aqueous system to which it is added. In most instances the polyelectrolyte would be added to an aqueous system as a component of a liquid formulation, rather than as a dry solid. The formulation would contain the inert tracer in a specific ratio to the polyelectrolyte.

In preferred embodiment, inert tracer(s) is not consumed or selectively lost to the water system, for instance due to degradation, deposition, complexation, or other phenomena. The inert tracer(s) used in the present invention is preferably substantially unconsumed in the use environment. Preferably, the inert tracer(s) is wholly inert in the water-system environment would not react to any significant extent with any of the components in the water system to which it is added, would not degrade in the environment of the water system and would be incapable of coupling and/or depositing in any manner within such water system. There are water-soluble inert tracer(s) that are wholly inert, or substantially inert, in the aqueous environments likely to be encountered in industrial water systems. Further, it is believed that inert tracer(s) having a degree of inertness such that no more than 10 weight percent thereof is lost due to reaction, degradation, coupling and/or deposition during the time that elapses between its addition and the sampling is sufficiently, or substantially, inert for the purpose of the present invention for most, if not all, tracer monitorings.

Among the substantially inert fluorescent compounds are the mono-, diand trisulfonated naphthalenes, including their water-soluble salts, particularly the various naphthalene mono-, di, and tri-sulfonic acid isomers, which are a preferred inert tracer(s) for use in the present invention. The naphthalene mono- and disulfonic acid isomers are water-soluble, generally available commercially and easily detectable and quantifiable by known fluorescence analysis techniques. Preferred naphthalene mono- and disulfonic acid isomers are the water-soluble salts of naphthalene sulfonic acid CNSA"), such as 1-NSA and 2-NSA, and naphthalene disulfonic acid ("NDSA" or "NDA"), for instance 1,2-NDSA, 1,3-NDSA, 1,4-NDSA, 1,5-NDSA, 1,6-NDSA, 1,7-NDSA, 1,8-NDSA, 2,3-NDSA, 2,4-NDSA and so forth. Many of these inert tracer(s) (mono-, di- and trisulfonated naphthalenes and mixtures thereof) are extremely compatible with the environments of most industrial water systems. Among these preferred fluorescent tracers, 2-NSA and 1,5-NDSA have been found to be thermally stable (substantially inert) at temperatures up to at least about 540° C. (1004° F.), for at least 24 hours at 285° C. (545° F.) and at pressures up to about 1,500 psig for time periods at least commensurate with, and often well in excess of, commercial water system holding times. Such inert fluorescent tracers are not selectively carried over into steam.

Another group of inert fluorescent compounds that are preferred for use in the process of the present invention are the various sulfonated derivatives of pyrene, such as 1, 3, 6, 8-pyrene tetrasulfonic acid, and the various water-soluble salts of such sulfonated pyrene derivatives.

The inert tracer may be a normal component of one of the formulated polyelectrolyte product, for instance one or more aromatic hydrocarbons of a hydrocarbon-containing formulated polyelectrolyte product, or it may be a tagged version of a normal component of one of the formulated polyelectrolyte product, but in most instances it would be a compound(s) added to the formulated polyelectrolyte product, or otherwise proportionally added to the water system, for the primary and/or sole purpose of being an inert tracer for the present process.

The inert tracer is at times referred to herein merely as a "tracer", and the functional "tracer" terminology is not used herein in reference to the fluorochromatic reagent unless expressly indicated otherwise. The fluorochromatic reagent would not generally be charged to a water system together or concomitantly with the polyelectrolyte treatment agent, nor would it follow the polyelectrolyte in the system, and thus in that sense not act as a tracer for the purposes of the present invention. The tracer is preferably selected from among those that are easily detectable by the fluorescence analysis method being employed in the process. Other analysis methods for use in detecting the inert tracer include HPLC and fluorescence analysis combinations, ion-electrode analysis, colorimetry analysis, transition metal analysis, statistical analysis, chemiluminescence, combinations of HPLC and other detection methods such as light absorbance analysis, post-column derivatization, conductivity and the like, some of which are described in more detail below.

The detection and quantification of specific substances by fluorescence emission spectroscopy is founded upon the proportionality between the amount of emitted light and the amount of a fluoresced substance present. When energy in the form of light, including ultraviolet and visible light, is directed into a sample cell, fluorescent substances therein will absorb the energy and then emit that energy as light having a longer wavelength than the absorbed light. The amount of emitted light is determined by a photodetector. In practice, the light is directed into the sample cell through an optical light filter so that the light transmitted is of a known wavelength, which is referred to as the excitation wavelength and generally reported in nanometers ("nm"). The emitted light is similarly screened through an optical filter so that the amount of emitted light is measured at a known wavelength or a spectrum of wavelengths, which is referred to as the emission wavelength and generally also reported in nanometers. When the measurement of specific substances or categories of substances at low concentrations is desired or required, such as often is the case for the process of the present invention, the optical filters are set for a specific combination of excitation and emission wavelengths, selected for substantially optimum low-level measurements, although the use of such excitation/emission wavelengths combinations are not limited to low level measurements.

In general, the concentration of an inert tracer(s) can be determined from a comparison of a sample's emissions intensity to a calibration curve of the given tracer(s)'s concentration versus emission(s) for the same set of excitation wavelength/emission wavelength(s). Such a concentration-by-comparison method by which the sensed emission(s) are converted to a concentration equivalent preferably is employed to determine concentrations of an inert tracer(s) that are within the concentration range over which a linear emission response is observed, and this concentration range is referred to herein as the "linear-emission-response concentration range". The linear-emission-response concentration range is to some extent dependent upon the specific inert tracer(s), the excitation wavelength/emission wavelength set employed and the engineering design of the fluorometer. At inert tracer(s) concentrations higher than a given inert tracer(s)'s linear-emission-response concentration range, there is a negative deviation from ideal (linear) behavior, the degree of emission for a given concentration being less than predicted by a linear extrapolation. In such instances, a correction can be applied to determine the concentration of the inert tracer(s) in the sample directly from the calibration curve, or the sample can be diluted by known factors until the concentration of the inert tracer(s) therein falls within the linear-emission-response concentration range. If the inert tracer(s) is present in the sample at only exceptionally low concentrations, for instance within a parts per trillion or lower range, there are techniques for concentrating the inert tracer(s) by known factors until its concentration falls within the linear-emission-response concentration range or is otherwise more readily measured, for instance by liquid extraction. Nonetheless, preferably a calibration curve over the linear-emission-response concentration range would be prepared or obtained before employing a given inert tracer(s), and preferably the inert tracer(s) would be added to the water of the water system in an amount sufficient to provide a concentration of the inert tracer(s) at the sampling point that is within the linear-emission-response concentration range, or will fall within the linear-emission-response range upon sample dilution or concentration. Generally the linear-emission-response concentration range of an inert tracer(s) is very broad and one can readily identify the amount of the inert tracer(s) that will be sufficient for this purpose. A linear-emission-response concentration range for an unmodified sample and typical standard equipment will most often extend at least through a concentration range of from a concentration of "m" to a concentration of at least 2,000 m.

A determination of the presence of a fluorescent inert tracer(s) and preferably the concentration thereof in a sample taken from a water system can be made when the concentration of the inert tracer(s) in the sample is only several parts per million (ppm) or even parts per billion (ppb) or parts per trillion (ppt) for some of the inert tracer(s) that can be employed in the process of the present invention. In preferred embodiment, the amount of a fluorescent inert tracer(s) added to the water system should be sufficient to provide a concentration of the inert tracer(s) in the sample to be analyzed of from 1 ppb to about 100 ppm. Such analyses, that is, the measurements of the light emitted in response to the light transmitted to the sample, can be made on-site, preferably on an almost instant basis or on a semi-continuous or continuous basis, with simple portable equipment, such as the photodetector and screens described above.

At times it is desired to employ a plurality of inert tracer(s). For instance, it may be desired to trace more than one polyelectrolyte, and to accomplish the sampling for each at about the same point downstream of the site(s) at which the polyelectrolytes were added. In such instance, a separate inert tracer may be used for each polyelectrolyte added. Such separate and distinct inert tracers can each be detected and quantified in a single water sample if their respective wavelengths of emission do not seriously interfere with one another. Thus concurrent analyses for multiple inert tracers is possible by selection of inert tracers having appropriate spectral characteristics. Preferably, separated wavelengths of radiation should be used to excite each of the inert tracers and their fluorescent emissions should be observed and measured at separated emission wavelengths, and a separate concentration calibration curve prepared or obtained for each inert tracer. In other words, more than one inert tracer can be employed, and then the presence and/or concentration of each such inert tracer in the water system should be determined using analytical parameters (particularly the excitation/emission wavelengths) effective for each such inert tracer, which analytical parameters preferably are sufficiently distinct to differentiate between measurements of other inert tracers and fluorochromatic reagents.

Fluorescence emission spectroscopy on a substantially continuous basis, at least over a given time period, is one of the preferred analytical techniques for the process of the present invention.

Fluorescence emission spectroscopy is one of the preferred analysis techniques for detecting and determining the concentration of the inert tracer in the process of the present invention. Fluorescence emission spectroscopy is the technique employed in the present invention for the determination of the fluorochromatic reagent concentration and, in many instances the use of the same technique for both the fluorochromatic reagent and the inert tracer is extremely convenient. Moreover, the fluorescence analysis technique is extremely advantageous. Fluorescent chemical tracers and monitoring techniques are now known, for instance as disclosed in U.S. Pat. No. 4,783,314, the disclosure of which is incorporated herein by reference, wherein inert fluorescent tracers are employed in combination with a fluorescence monitoring, such as the sodium salt of 2-naphthalenesulfonic acid and Brilliant Acid Yellow 8G dye.

In general, for most fluorescence emission spectroscopy methods having a reasonable degree of practicality, it is preferable to perform the analysis without isolating in any manner the inert tracer and/or fluorochromatic reagent. Thus there may be a minor degree of background fluorescence in the sample on which the fluorescence analysis is conducted, which background fluorescence may come from chemical compounds in the water system that are unrelated to the present process. In preferred embodiment, the fluorochromatic reagent and inert tracer are selected to avoid one producing background fluorescence for the other. In instances where the background fluorescence is low, the relative intensities (measured against a standard fluorescent compound at a standard concentration and assigned a relative intensity for instance 100) of the fluorescence of the tracer and/or fluorochromatic dye versus the background can be very high, for instance, a ratio of 100/10 or 100/2 when certain combinations of excitation and emission wavelengths are employed even at low fluorescent compound concentrations, and such ratios would be representative of relative performance (under like conditions) of respectively 10 and 50. In preferred embodiment, the excitation/emission wavelengths and/or the amount of tracer employed are selected to provide a relative fluorescene of at least about 5 or 10 for the given background fluorescence anticipated.

For instance, for most cooling, boiler and other industrial water backgrounds, a compound that has a relative performance of at least about 5 at a reasonable concentration is very suitable as an inert tracer. When there is or may be a specific chemical specie of reasonably high fluorescence in the background, the tracer and/or fluorochromatic reagent and/or the excitation and/or emission wavelengths often can be selected to nullify or at least minimize any interference of the tracer and/or fluorochromatic reagent measurement(s) caused by the presence of such specie.

One method for the continuous on-stream monitoring of chemical tracers such as the inert tracer by fluorescene emission spectroscopy and other analysis methods is described in U.S. Pat. No. 4,992,380, the disclosure of which is incorporated hereinto by reference.

The combination of high-pressure liquid chromatography ("HPLC") and fluorescene analyses of fluorescent tracers is a powerful tool for the present process, particularly when very low levels of the inert tracer are used or the background fluorescene encountered would otherwise interfere with the efficacy of the fluorescence analysis. The HPLC-fluorescence analysis method allows the tracer compound to be separated from the fluid matrix and then the tracer concentration can be measure. The combination of HPLC-fluorescene analysis is particularly effective for measuring minute levels of tracer in highly contaminated fluids.

The HPLC method can also be effectively employed to separate a tracer compound from a fluid matrix for the purposes of then employing a tracer-detection method other than fluorescence analysis, and such other tracer-detection methods include without limitation light absorbance, post-column derivatization, conductivity and the like.

Colorimetry or spectrophotometry may be employed to detect and/or quantify an inert tracer. Colorimetry is a determination of a chemical specie from its ability to absorb ultraviolet or visible light. One colorimetric analysis technique is a visual comparison of a blank or standard solution (containing a known concentration of the tracer specie) with that of a sample of the fluid being monitored. Another colorimetric method is the spectrophotometric method wherein the ratio of the intensities of the incident and the transmitted beams of light are measured at a specified wavelength by means of a detector such as a photocell or photomultiplier tube. Using a colorimetric probe, a fiber optic (dual) probe, such as a Brinkman PC-80 probe (570 nm filter), a sample solution is admitted to a flowcell in which the probe is immersed. One fiber optic cable shines incident light through the sample liquid onto a mirror inside the cell and reflected light is transmitted back through the sample liquid into a fiber optic cable and then to the colorimetric analyzer unit, which contains a colorimeter, by the other cable. The colorimeter has a transducer that develops an electrical analog signal of the reflected light characteristic of the tracer concentration. The voltage emitted by the transducer activates a dial indicator and a continuous line recorder printout unit. A set point voltage monitor may be employed to constantly sense or monitor the voltage analog generated by the colorimeter, and upon detection of a tracer signal (described below), a responsive signal may be transmitted to a responsive treatment agent feed line to commence or alter the rate of feed. Such a colorimetric analysis technique and the equipment that may be employed therefor are described in U.S. Pat. No. 4,992,380, the disclosure of which is incorporated hereinto by reference. Chemical tracers suitable for use in conjunction with a colorimetric technique include transition metals and substances which show light absorbance which is detectable from that of other species present in the system fluid or substances which react with color-forming reagents to produce light absorbance which is detectable from that of other species present in the system fluid.

According to another embodiment of the invention, an ion selective electrode may be used to determine the concentration of an inert chemical tracer through the potentiometric measurement of specific ionic tracers in aqueous systems. These electrodes respond only to selected ionic materials and gases dissolved in liquids, and hence such tracers must be ionized (or dissolved gases) in the environment in which they are to be determined. Ion selective electrodes work like pH electrodes, depending on a potential developed across a thin membrane by the difference in the concentrations of the ion (or gas) to be measured on each side of the ionically conducting thin layer. The concentration within the electrode is fixed and the potential varies with the concentration of ions (or gas) in the same. By calibration (the potential or current versus the concentration), the ionic (or gas) concentration at the sample electrode can be indexed to a reference or standard electrode that is insensitive to the tracer ion. To provide continuous monitoring of the tracer, the electrodes may be dipped directly into a stream of one of the fluids (collectively comprising a flow cell), or the fluid being monitored may be passed through an external flow cell into which the ion-selective and reference electrodes have been inserted. An ion selective electrode tracer monitoring technique and the equipment therefor are described in U.S. Pat. No. 4,992,380, the disclosure of which is incorporated hereinto by reference.

A transition metal compound (transition metal ions, oxy-anions, cations and associated complexes) can be quantitatively measured by one or more of known techniques. Preferred techniques include the colorimetry analysis and ion-selective electrode analysis described above. Another technique is molecular absorption. Molecular absorption in the ultraviolet and visible region depends on the electronic structure of the molecule. The energy absorbed elevates electrons from orbitals in a lower-energy state to orbitals in a higher-energy state. A given molecule can absorb only certain frequencies because only certain states are possible in any molecule and the energy difference between any ground and excited state must be equal to the energy added. At a frequency that is absorbed by a molecule, the intensity of the incident energy is greater than the intensity of the emergent energy, and is a measure of the absorbance. A sample of the fluid being monitored may be compared to a calibration curve (absorbance versus concentration) prepared from standard solutions containing known concentrations of the transition metal (or other suitable tracer specie) to detect and determine the concentration of the tracer. A molecular absorption technique for transition metal tracers is described in U.S. Pat. No. 4,992,380, incorporated hereinto by reference.

Analytical techniques for detecting the presence and/or concentration of a chemical specie without isolation thereof are within an evolving technology, and the above survey of reasonable analytical techniques for use in monitoring the inert tracer in the process of the present invention may presently not even be exhaustive, and most likely techniques equivalent to the above for the purposes of the present invention will be developed in the future.

An inert tracer may be selected for a given process based on a preference for one or more analytical techniques, or an analytical technique may be selected for a given process based on a preference for one or more inert tracers.

As noted above, in preferred embodiment, the chemical compound(s) selected as the inert tracer is soluble in the water system to which it is added and is stable in the environment thereof for the useful life expected of the inert tracer, particularly when it is desired not merely to detect the presence of some amount of the inert tracer, but also to determine the concentration thereof, or change in concentration. In preferred embodiment, the combination of the chemical compound(s) selected as the inert tracer and the analytical technique selected for determining the presence and/or concentration of such tracer, should permit such determination(s) without isolation of the inert tracer, and more preferably should permit such determination(s) on a continuous and/or on-line basis.

In a preferred embodiment the process of the present invention includes the addition an inert tracer to the aqueous system and monitoring the concentration of such tracer by an analytical technique effective for such tracer.

The concentration of an inert tracer added to the system in proportion to a polyelectrolyte is also a measure of the impact of any adjustments of system controls to regulate the in-system concentration of the polyelectrolyte, particularly when a plurality of adjustments are made concomitantly. For instance, if the goal is a 20 percent change (decrease/increase) in the concentration of the polyelectrolyte in the system, and the chosen control adjustment is a temporary change (decrease/increase) the blowdown from the system with a concomitant fresh water replacement, the inert tracer monitoring will disclose when the goal has been met as to the dilution mechanism, but, of course, not as to any polyelectrolyte selective impacts on its concentration during the time interval. The greater the complexity of the nonselective influences on in-system concentration, the more useful is the use of an inert tracer to track the net effect of these influences. Nonetheless the complimentary monitoring of an inert tracer may be extremely advantageous even when relatively simple control adjustments are made or when quantitative data is not determined. For instance, when the polyelectrolyte or system demand and/or system consumption monitoring indicates that an increase in polyelectrolyte in-system concentration is needed, a monitoring of a tracer in the system may be used to confirm that an upward adjustment of zero-consumption in-system concentration of the polyelectrolyte has been made, without quantifying the in-system concentration of the polyelectrolyte before and/or after the adjustment.

A "feed rate" monitoring for the inert tracer of a traced water treatment product is at times a preferred additional procedure, for instance by monitoring the tracer's concentration in a feed line upstream of the point at which the product is delivered to the system. Such "feed rate" monitoring is used to more precisely determine the actual amount of product being added to the system when the tracer is monitored in the feed line. The regulating of the in-system concentration of the present invention might combine at least some of the information provided by the monitoring of a tracer(s) upstream or downstream of the feed inlet to the water system with at least some of the information available concerning the concentration of the tracer(s) in the product feed.

The regulating of a polyelectrolyte in-system concentration may include any of a number of determinations based on monitoring of one or more inert tracers, which values may be relative values, substantially quantitative values, or approximate quantitative values. The proportion between a tracer and the active polyelectrolyte as fed to a water system need not be known provided the proportion is constant, or instead the proportion can change provided sufficient information is available to correlate the monitorings over the desired time period.

A water treatment product feed is commonly, but not always, comprised of one or more active water treatment agents and one or more inert diluents. A diluent is frequently a solvent for the water treatment agent(s), and such solvent can be, and in many instances is, water. A diluent is frequently included in the water treatment agent feed to facilitate the rapid and substantially homogeneous distribution of the active water treatment agent(s) in the water system to which the water treatment agent feed is charged. The concentration of the active water treatment agent(s) in a water treatment product feed is generally from about 0.5 to about 50 weight percent and at times higher, part or all of which could be a polyelectrolyte. The weight ratio of polyelectrolyte to tracer in the water treatment product feed might often be within the range of from about 10:1 to about 1000:1. The weight ratio between the polyelectrolyte and the tracer in a system ahead of any selective polyelectrolyte-consuming site is of course substantially the same as that of the water treatment product feed, and thereafter that weight ratio would fall as the polyelectrolyte is selectively consumed in the water system, for instance to the extent of approaching a 1:1 weight ratio or less.

Although the tracer used in the present invention is generally an inert tracer, a tracer that is an active treatment agent in one system may be a substantially inert tracer in another system. An active tracer may be, for instance, a corrosion inhibitor. One series of compounds applied to reduce copper and copper-alloy corrosion are aromatic organic corrosion inhibitors. This series of organic compounds, which includes benzotriazole ("BT"), butylbenzotriazole ("BBT"), tolyltriazole ("TT"), and related compounds, react with the metal surface and form protective films on copper and copper alloys. These compounds are active corrosion inhibition treatment components and are referred to generally herein as copper corrosion inhibitors or corrosion inhibitors, or as aromatic azoles, and at times as triazoles or aromatic(thio)(tri)azoles.

The preferred analytical technique for aromatic(thio)(tri)azoles when used as an active tracer in the process of the present invention is fluorescence emission spectroscopy. Some water systems have no copper, copper alloy or other metal surfaces that require protection from a corrosion inhibitor, and for such systems the use of copper corrosion inhibitors as inert tracers for the purposes of the present invention would generally not be a common embodiment of the invention. The use of copper corrosion inhibitors may nonetheless be a preferred embodiment in such systems when they are already contained in waters that will make up at least a portion of the water treatment agent feed stream or when water from the system will be recycled to a system that needs such corrosion inhibitor. For instance, some industries may recycle water from one water system, such as a cooling tower, through another water system. In such instances, if these copper corrosion inhibitors were added to the water of the first water system for corrosion inhibition and/or active tracer performance, they may be present in the water treatment agent feed and/or makeup water stream of the second water system in sufficient concentration for the purposes of the present invention. Further, if the second water system contains no metal surfaces which lead to consumption of such copper corrosion inhibitors, or at least no such metal surfaces upstream of relevant monitorings, such normally "active" tracers are inert tracers for the purposes of the present invention.

The use of other nonpreferred tracers may similarly become a preferred embodiment of the present invention when they are already contained in waters that will make up at least a portion of the water treatment product feed stream or when the tracer-containing effluent water will be recycled to a system that employs such tracer as a tracer or for other purposes, such as treatment purposes.

As noted elsewhere herein, polyelectrolytes employed as active water treatment agents include scale inhibitors, corrosion inhibitors, dispersants, surfactants, antifoaming agents, flocculants and the like, and are not limited to these categories. These polyelectrolyte water treatment agents may be, but are not limited to, synthetic water-soluble polymers. The following descriptions of polyelectrolyte water treatment agents are representative, and not meant to be limiting.

A scale inhibition program commonly employs a multi-component inhibitor, for instance a phosphonate together with a polymeric crystal modifier/dispersant, although single active-component products and all-polymer programs are well known. The polymeric scale inhibitor species most commonly used are polyelectrolytes such as maleic acid polymers and their salts, (meth)acrylic acid polymers and their salts, sulfonated polymers such as polymers containing sulfonated styrene or sulfonated N-alkyl substituted (meth)acrylamide mer units and their salts, and polymers comprised of a plurality of anionic mer unit species.

Phosphonates (organophosphorus compounds) such as amino-tri(methylene phosphonate) (AMP) and hydroxyethylidene-1,1-diphosphonate (HEDP) are employed as crystal growth inhibitors or modifiers (threshold inhibitors which virtually increase the solubility of calcium carbonate by mechanism not well understood). Phosphonates are not "polyelectrolytes" as that term is used herein, and as understood generally in the field, but their presence in a water system is believed be harmless to the present invention. The various phosphonates will not provide any significant degree of fluorochromatic response, nor any interference to the fluorochromatic response of the polyelectrolyte component.

Low molecular weight, highly charged anionic polymers are employed as crystal lattice distortion agents, inhibiting the growth of scale-species microcrystals. Crystal growth inhibitors, crystal lattice distortion agents, and other scale inhibitors that increase the solubility of the scale species or otherwise reduce scaling tendencies by influencing the morphology and/or growth rate of the growing crystals, and thereby delaying precipitation, are at times referred to as "stabilizers", and their mechanism(s) as "stabilization". Larger anionic polymers are employed as dispersants, preventing scale particles from agglomerating further, primarily by a charge repulsion mechanism. Such anionic polymers, as noted above, generally have carboxylic and/or sulfonic acid functionality. These species of inhibitors commonly are effective in sub-stoichiometric amounts.

The scale inhibitors generally ionize to negatively charged species. The anionic group of the maleic acid and (meth)acrylic acid polymers is the carboxylate anion ($—COO—$). The anionic group of sulfonic acid polymers is the sulfonate anion ($—SO_3—$) and that of the phosphonates is the phosphonate anion ($—PO_3=$). These and like anionic groups are the active sites in scale inhibition. The molecular weight of an anionic polymeric scale inhibitor is sometimes limited by a ceiling at which the species begins to act as a bridging agent, and at other times polymeric flocculants having no such maximum as to their molecular weight may be included in formulations. The molecular weight of an anionic polymeric scale inhibitor might be limited by a lower limit, below which the polymer's molecular weight is too low to provide effective crystal modification activity. Anionic polymeric scale inhibitors often have weight average molecular weights of less than about 10,000, although polymeric anionic (or highly polar) scale inhibitors having weight average molecular weights of 20,000 or higher, even up to about 100,000, are available, and scale inhibition activity has been seen in anionic polymer having weight average molecular weights up to about 200,000 and even 300,000. Poly(meth)acrylic acid scale inhibitors commonly are within the weight average molecular weight range of from about 500, or 1,000, to about 20,000. Polymaleic acid scale inhibitors, which have the potential for a higher charge density than poly(meth)acrylic acid scale inhibitors, commonly are within the weight average molecular weight range of from about 500, or 700, to about 10,000.

The molecular weight range of a polymer water-treatment species in which water-treatment activity is optimized is dependent upon a variety of factors, including without limitation, the charge density, type and orientation of ionic sites, the existence of groups that sterically hinder the ionic sites, conformation of the species on a molecular level under the existing use environment, and the like. Thus the weight average molecular weight range for water-treatment activity is dependent upon the polymer's structural characteristics and at times the environment in which it is to function. The molecular weight of a polymeric water-treatment agent generally is the molecular weight that provides a polymer having an effective water-treatment effect. The effective molecular weight of anionic polymeric water treatment agents is often from about 500 to about 300,000, and in some applications the polymer has a weight average molecular weight of less than about 10,000 or 20,000, particularly when anionic mer units of the scale inhibitor are predominantly carboxylate anion containing mer units or when carboxylate anion containing mer units comprise more than 50 mole percent of the polymer.

Polymeric scale inhibitors often, but not always, have an anionic charge density of at least about 10 mole percent, and commonly at least about 20, or 25, mole percent of mer units containing at least one such anionic site, such mer units being segments of the polymer(s) containing two backbone carbons. Many scale inhibitor polymers have an anionic charge density of at least about 50 mole percent, and even at least about 80 to 100, mole percent of mer units containing at least one such anionic site.

The anionic mer units of some polymeric water-treatment agents have the chemical structure I:

Chemical Structure I wherein R is hydrogen or methyl, $R_1$ is hydrogen or —COX, and A is an aromatic sulfonate or —COX, wherein X is —OM or

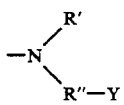

wherein M is alkyl (usually but not necessarily a lower alkyl), hydrogen or another single-valent cation, such as sodium, potassium, ammonium, lithium, and the like, wherein R" is hydrogen or lower alkyl having from about 1 to 7 carbon atoms and where R" is a lower alkyl having from about 1 to 7 carbon atoms, and wherein Y is sulfonate, (poly)hydroxy, (poly)carboxyl or carbonyl and combinations thereof. The lower alkyl radicals include methyl, ethyl, propyl, isopropyl, butyl, sec-butyl, pentyl, iso-pentyl, hexyl and other isomers of these lower alkyls. The aromatic sulfonates include without limitation sulfonated benzyl and mono-, di- and trisulfonated naphthyl. This type of anionic mer units are generally derived from ethylenically-unsaturated monomers, which may be further derivatized by post-polymerization derivatization techniques, many of which are known to those or ordinary skill in the art.

The polymeric water-treatment agents (scale inhibitors, dispersants, corrosion inhibitors and the like) may have mer units other than anionic mer units, such as (meth)acrylamide mer units and (meth)acrylamide mer units containing lower alkyl substituents and the amide nitrogen, such as t-butyl (meth)acrylamide and other mer units that may be incorporated into these polyelectrolyte without undue loss of the required water treatment activity and water solubility.

Anionic water treatment polymers are of course not limited to those derived from addition polymerization methods, and anionic water treatment polymers further include condensation polymers including, but not limited to, formaldehyde condensation polymers such as urea-formaldehyde polymers.

U.S. Pat. No. 4,801,388, D. W. Fong, John E. Hoots, and Donald A. Johnson, issued Jan. 31, 1989, incorporated hereinto by reference, describes water-soluble polyelectrolytes which are effective as scale inhibitors and dispersants, and methods for preparing such polyelectrolytes by post-polymerization derivatization. Such polyelectrolytes are exemplitive of the wide range of mer unit types that may be included in a polymeric scale inhibitor. The amount of such polyelectrolytes used in an aqueous system is described as preferably in the range of from about 1 to about 200 ppm.

U.S. Pat. No. 4,869,828, incorporated hereinto by reference, describes water-soluble polyelectrolytes which are effective as stabilizers for iron oxide and iron hydroxide in aqueous systems; and reduces or eliminates the deposit of such species. The amount of such polyelectrolytes used in an aqueous system may be in the range of from about 1 to about 50 ppm.

U.S. Pat. No. 4,963,267, incorporated hereinto by reference, describes water-soluble polyelectrolytes which are effective as stabilizers for precipitate species of manganese in aqueous systems, and reduces or eliminates the deposit of such species. Such polyelectrolytes have pendant N-substituted alkyl-sulfonate amide groups. The amount of such polyelectrolytes used in an aqueous system may be in the range of from about 0.1 to about 50 ppm.

U.S. Pat. No. 4,919,821, incorporated hereinto by reference, describes a method for inhibiting scale in using water-soluble polyelectrolytes having pendant N-substituted maleamic mer units, N-substituted maleimide mer units and maleic acid mer units.

U.S. Pat. No. 5,035,806, incorporated hereinto by reference, describes polyelectrolytes that are effective scaling salt threshold inhibitors and dispersants that include pendant carboxylate, N-substituted sulfoalkyl amide and N-substituted alkyl amide groups. Such polyelectrolytes have molecular weights within the range of from about 3,000 to about 50,000, and a preferred in-system concentration thereof to a water system is the amount sufficient to provide a polyelectrolyte concentration of from about 1 to about 100 ppm.

U.S. Pat. No. 4,923,634, incorporated hereinto by reference, describes a method for inhibiting corrosion in using water-soluble polyelectrolytes having pendant carboxylate and N-substituted acrylamide mer units which are used in aqueous systems together with water-soluble inorganic phosphate and optionally phosphonate and/or azole species. These polyelectrolytes may have weight average molecular weights within the range of from about 1,000 to about 150,000 and charge densities substantially commensurate with polyelectrolyte scale inhibitor/dispersants. Such polyelectrolytes have pendant N-substituted alkylsulfonate amide groups. The amount of such polyelectrolytes used in an aqueous system may be in the range of from about 0.1 to about 50 ppm.

U.S. Pat. No. 5,002,697, incorporated hereinto by reference describes a process for inhibiting corrosion of metals in contact with aqueous systems with a water treatment composition comprising a source of molybdate ion and a water-soluble polyelectrolyte containing pendant amide functionality. The useful polyelectrolytes primarily are copolymers or terpolymers of acrylamide and/or N-substituted alkyl derivatives thereof with acrylic acid and/or its homologs, which preferably have molecular weights within the range of from about 500 to about 100,000, and are employed in aqueous systems at concentrations of from about 0.5 to about 200 ppm.

In one embodiment of the present invention, the polyelectrolyte being monitored preferably is comprised of from about 0 to 95 mole percent of (meth)acrylamide mer units, which are nonionic, but polar, mer units, and from about 5 to about 100 mole percent of anionic mer units. The anionic mer units may contain pendant carboxyl radicals, such as the mer units derived from (meth)acrylic acid, itaconic acid, maleic acid, crotonic acid and the like, and salts thereof with monovalent cations ("monovalent salts thereof), particularly sodium salts thereof, and preferably such anionic mer units are in a monovalent salt form. The anionic mer units may be N-sulfoalkyl (meth)acrylamide mer units, which provide a pendant sulfonate radical. When the polyelectrolyte is an acrylamide polymer, it often is comprised of at least 5, or 10, mole percent of N-sulfoalkyl (meth)acrylamide mer units or anionic acrylate mer units or combinations thereof.

U.S. Pat. No. 4,678,840 describes a method for preparation acrylamide polymers having ionizable phosphonate groups, and the disclosures of this patent are incorporated hereinto by reference. Phosphonate-containing acrylamide polymers that meet the preferred molecular weight ranges may possibly be as active in water treatment processes as other preferred anionic acrylamide polymers described above.

The polyelectrolyte may be cationic. For instance, the polyelectrolyte may be a vinyl addition polymer comprised of (meth)acrylamide mer units and cationic mer units, which often are the quaternary ammonium salt type, such as the quaternized salts of mer units of N-alkylsubstituted aminoalkyl esters of acrylic acid and others, including, for example:

1. the quaternized salts of reaction products of a polyamine and an acrylate type compound prepared, for example, from methyl acrylate and ethylenediamine;
2. (methacryloyloxyethyl)trimethyl ammonium chloride;
3. diallylmethyl(beta-propionamido)ammonium chloride, (betamethacryloyloxyethyl)trimethylammonium methyl sulfate, and the like;
4. quaternized vinyllactam;
5. the quaternized salt of vinylbenzyltrialkylamines such as, for example, vinylbenzyltrimethylammonium chloride;
6. quaternized salt of vinyl-heterocyclic monomers having a ring nitrogen, such as (1,2-dimethyl-5-vinylpyridinium methyl sulfate), (2-vinyl-2-imidazolinium chloride) and the like;
7. dialkyldiallylammonium salt including diallyldimethyl ammonium chloride ("DADMAC");
8. methacrylamidopropyltrimethylammonium chloride ("MAPTAC");

Cationic polyelectrolytes are often vinyl addition polymers containing up to mole percent of such cationic mer units, and commonly from about 5 up to about 30, or 40, mole percent thereof. A preferred cationic mer unit for water treatment polymers is DADMAC. A preferred cationic polymer for water treatment applications is substantially comprised of acrylamide and DADMAC.

Cationic polyelectrolytes are not limited to those having pendant quaternary ammonium salt groups, and instead include cationic acid salts such as dimethylaminoethylmethacrylate sulfuric acid salt.

Vinyl addition polymers comprised of (meth)acrylamide mer units, anionic acrylate mer units and N-sulfoalkyl (meth)acrylamide mer units may be directly synthesized from the corresponding monomers by known techniques, for instance using as the sulfonate-containing monomer the 2-(meth)acrylamido-2-methylpropane sulfonic acid, or the methacrylamide version thereof. N-sulfoalkyl (meth)acrylamide mer units can also be incorporated into an existing polyelectrolyte by post-polymerization derivatization, for instance by one of the methods described in U.S. Pat. No. 4,762,894, U.S. Pat. No. 4,680,339, U.S. Pat. No. 4,795,789, and U.S. Pat. No. 4,604,431, the disclosures of all of which are hereby incorporated hereinto. The sulfonated mer units of such post-polymerization derivatized polymers are generally of the sulfonate N-alkyl substituted (meth)acrylamide type.

The polyelectrolyte being monitored by the method of the present invention preferably is substantially linear and substantially free of pendant hydrophobic radicals or hydrophobic polyelectrolyte backbone segments, but the present invention does not exclude the use of polymers having some branching or cross-linking, or some hydrophobic moieties, provided the polyelectrolyte retains its water solubility.

An amphoteric polyelectrolyte also is not excluded for use in the present process. Generally an amphoteric polyelectrolyte having a predominance of either anionic or cationic mer units and are sufficiently water-soluble and retain a sufficient degree of polyelectrolyte characteristic to be monitored by the process of the present invention. Preferably the mole ratio between the predominant electrolytic mer units and those of opposite charge is no less than about 8:20 and more preferably is no less than about 9:10.

The polyelectrolyte actives target in industrial water treatment programs is generally amount sufficient to provide an effective degree of water-treatment activity, for instance such as scale and/or corrosion inhibition. The in-system concentration of a polyelectrolyte product effective to control scale-deposit or corrosion formation in the various industries varies of course with the industry standards, the water or brine properties, the water system peculiarities, temperatures, the polyelectrolyte characteristics (including without limitation their molecular weight, their molecular weight distribution, charge density, the functional group providing the charge and the like), the concentration of polyelectrolyte actives in the product and other variables. Maintenance dosages for some aqueous systems range from about 1 ppm or less (for instance down to about 0.1 ppm) to about 50 ppm, based on parts by weight of the polyelectrolyte actives per million parts by weight of the water system to which it is being fed, and other aqueous systems require dosages of 100 ppm, or 150 ppm, same basis, or even higher, such as 100 to 200 ppm, may be required.

The polyelectrolyte monitored in the present invention should be water soluble at the concentration at which it is employed in the water system. A polyelectrolyte having a molecular weight much higher than is commonly found among water treatment polyelectrolytes may be monitored by the method of the present invention. For instance, a polyelectrolyte that is a vinyl addition polymer may have a weight average molecular weight up to 500,000, and up to even about 1,000,000, and at times even up to 4,000,000, or 5,000,000. The polyelectrolyte being monitored has no molecular weight ceiling for the purposes of the present invention, and some polyelectrolytes having molecular weights of 15,000,000 or higher are believed capable of being monitored by the method of the present invention. Such water solubility characteristic generally does not create a molecular weight ceiling because even acrylamide homopolymers, substantially free of any electrolytic groups, meet such a standard at the high molecular weights that can now be provided by conventional synthesis techniques, provided the polymer is substantially linear, and the presence of ionic mer units would increase the water solubility of a polyacrylamide.

The limitations as to the polyelectrolyte that can be monitored by the present invention by determining its fluorochromatic response, or by determining its fluorochromatic response and by tracking the concentration of the polyelectrolyte added to the system with an inert tracer, are few.

In all instances wherein the concentration of the component is expressed in terms of weight percentage of the aqueous solution or of the composition, the percentage is based on total weight of the aqueous solution or composition including all other additives thereto.

As noted above, the fluorochromatic analysis of the present process is selective for polyelectrolytes. There is no interference from a nonpolymeric surface active agent, such as a surfactant, dispersant, or detergent, in the process of the present invention. The terminology "nonpolymeric surface active agent" as used herein, and generally, means chemical species that have distinct hydrophilic and hydrophobic sections. Such agents are not polymeric except for sections thereof that have repeating alkoxylated units, such as ethylene oxide or propylene oxide sections. While a broad definition of surface active agent may in some instances include polymers such as the polyelectrolytes of the present invention, the terminology of nonpolymeric surface active agent does not include such polymers. As a generality, one can distinguish such species by absence of repeating units (which may be of course randomly distributed) and/or molecular weight. As to repeating units, nonpolymeric electrolytic surface active agents (or other nonpolymeric electrolytes) would not have a plurality of repeating ionic units. As to molecular weight, nonpolymeric electrolytic surface active agents (or other nonpolymeric electrolytes) would not have molecular weight exceeding about 2,500.

The fluorescent reagents used in the following Examples, unless expressly indicated otherwise, are commercially available from Aldrich Chemical Company, Inc., Milwaukee, Wis.

EXAMPLE 1

The change in the Percent Relative Fluorescence of the cationic reagent (pinacyanol chloride) (FW 388.94 and maximum absorption wavelength of 604 nm and a secondary but strong absorption wavelength of 560 nm) in the presence of an anionic polymer was determined as follows. A dilute aqueous solution of pinacyanol chloride was prepared by diluting 5 ml of a commercial pinacyanol chloride formulation to 100 ml with deionized water ("DI water"). The commercial pinacyanol chloride formulation contained a concentration of pinacyanol chloride of 0.125 g/l, and thus the concentration of pinacyanol chloride in the diluted solution was $1.8 \times 10^{-5}$ moles per liter. Samples of the diluted pinacyanol chloride solution were admixed with aqueous solutions containing from 0 to 9 ppm of a commercial anionic polymeric dispersant, as actives. The fluorescence intensity of each sample was then determined using an excitation wavelength of 335 nm and an emission wavelength of 435 nm. The sample containing no anionic polymer was assigned a Percent Relative Fluorescence of 100, and a Percent Relative Fluorescence ("PRF") for each other sample was determined in comparison to this standard. Then a Percent Relative Fluorescence Change ("PRFC") for each sample was calculated using the formula below. The Percent Relative Fluorescence and Percent Relative Fluorescence Change for each sample are set forth below in Table 1, the samples being identified as to the concentration of the anionic polymer in the solution admixed with the cationic fluorescent reagent dye solution.

TABLE 1

| Concentration of Anionic Polymer (ppm) | Percent Relative Fluorescence (PRF) | Percent Relative Fluorescence Change (PRFC) |
|---|---|---|
| 0 | 100 | 0 |
| 1 | 79 | 21 |
| 2 | 54 | 46 |
| 3 | 24 | 76 |
| 4 | 21.3 | 78.7 |
| 9 | 15 | 85 |

A plot of the Percent Relative Fluorescence Change versus concentration of anionic polymer is shown in FIG. 1. As best seen from FIG. 1 and Table 1, the fluorescence intensity of the pinacyanol chloride reagent diminishes as it complexes with the anionic polymer, and thus the fluorescence intensity decreases in inverse proportion to the amount of anionic polymer with which it was admixed. As the concentration of anionic polymer increased, the amount of anionic polymer available for polyelectrolyte/reagent interaction increased, and the Relative Percent Fluorescence Change increased. This fluorochromatic response was substantially linear until a point at which the response leveled off at about 3 ppm anionic polymer. At this point the pinacyanol chloride was exhausted, and more pinacyanol chloride would have been required to continue the linear response of the pinacyanol chloride fluorescence to the increasing amounts of anionic polymer. The anionic polymer had an anionic charge density of about 80 mole percent (mer units of average molecular weight of 86). The point at which the pinacyanol chloride was exhausted was therefore at a mole ratio of anionic mer units to pinacyanol chloride of about 1.35:1, which is a molar excess of anionic mer units of about 50 percent. It was also noted that while a precipitate formed later in the solutions that contained both the pinacyanol chloride and the anionic polymer, it was not an adherent precipitate and did not stick to the walls of the glassware or cuvettes used.

EXAMPLE 2

Figure 2:
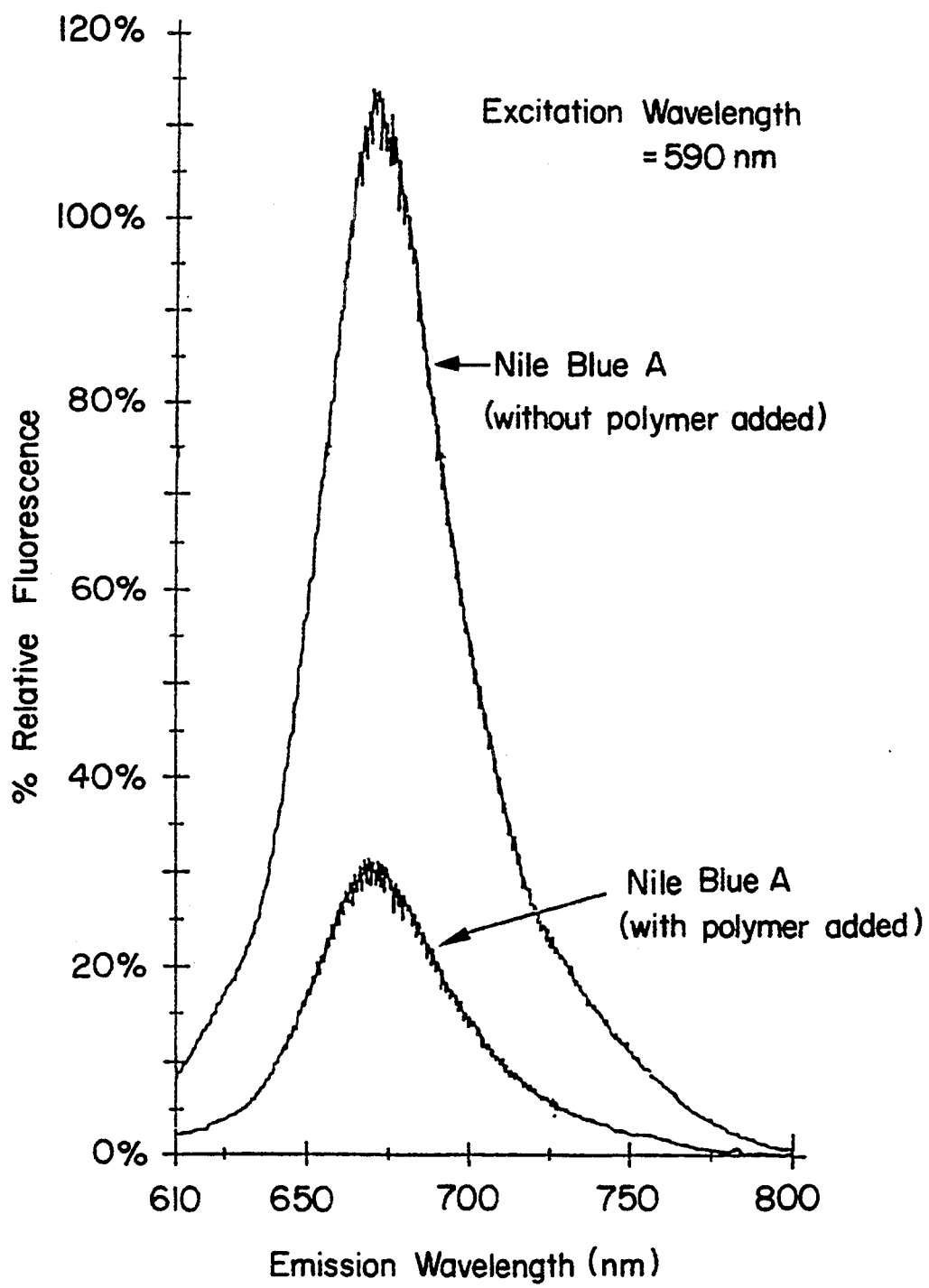
FIG. 2 is a plot showing the fluorescence spectrums of an aqueous solution of a cationic fluorochromatic reagent and an aqueous solution of such fluorochromatic reagent and an anionic polymer.

The fluorescence spectrum along the wavelength region from 610 to 800 nm was determined for an aqueous solution of the cationic fluorescent reagent Nile Blue A (FW of 732.84 and absorption maximum at 633 nm) alone and in the presence of an anionic polymeric water treatment agent, using an excitation wavelength of 590 nm. These spectra are shown superimposed for comparison in FIG. 2, the spectra being differentiated by line type and labeled as to whether the sample was with or without the polymer. In FIG. 2 a dramatic decrease in the size of the fluorescence emission peak (centered about the 675 nm wavelength) can be clearly seen when the anionic polymer was admixed with the Nile Blue A reagent. The decrease in the relative fluorescence intensity at this normal emission wavelength peak was about 80 percent.

Sufficient levels of some compounds (e.g., $Ca^{+2}$ and $Mg^{+2}$ hardness) can interfere with the interaction of metachromatic and fluorochromatic dyes with polymers. Using specific types of masking agents (e.g., chelants for hardness) in combination with the fluorochromatic dye reagent can significantly improve the application ranges of the analysis method (Table 2). Two suitable masking agents are phosphonobutanetricarboxylic acid (PBTC) and ethylenediaminetetraacetic acid (EDTA) neutralized to pH 7 with aqueous sodium hydroxide. In the presence of calcium and/or magnesium and absence of masking agent, the fluorochromatic response between the dye reagent and anionic polymer is hindered (compare sample 2B with 2C and 3B with 3C). The addition of PBTC or EDTA allows virtually complete fluorochromatic response (94–98% recovery) between dye reagent and anionic polymer in presence of calcium and/or magnesium (compare sample 2C with 2D and 3C with 3D).

EXAMPLE 3

The change in fluorescence of the cationic fluorescent reagent Nile Blue A (FW of 732.84) was determined alone and in the presence of combinations of anionic polymeric water treatment agent, hardness ($Ca^{+2}$ or $Mg^{+2}$) and/or chelant (PBTC or EDTA). The anionic polymer was added first and concentration is listed as actives equivalent in 1 mL volume (column 2 of Tables 2–3). Next, chelant (at pH 7) was added in concentration listed as actives equivalent in 1 mL volume (column 4 of Tables 2–3). Then, bicarbonate alkalinity (200 ppm, as $CaCO_3$) and hardness ($Ca^{+2}$ or $Mg^{+2}$, column 3 of Tables 2–3) were added as $CaCO_3$ equivalent in 1 mL volume. Sample volume was diluted to 9 mL, and finally 1 mL Nile Blue A (0.0619 g/mL) was added. % Relative Fluorescence Change (excitation@670 nm and emission@690 nm) was taken after 3 minutes. The results are summarized in Tables 2–3.

TABLE 2

| Sample # | Dosage of Anionic Polymer (ppm) | Hardness Dosage (ppm) | Chelant (ppm) | % Relative Fluorescence Change (PRFC) |
|---|---|---|---|---|
| 2A | 0 | 0 $Ca^{+2}$ | 10,000 PBTC | 0% |
| 2B | 5 | 500 $Ca^{+2}$ | 0 PBTC | 5.0% |
| 2C | 5 | 500 $Ca^{+2}$ | 10,000 PBTC | 27.1% |
| 2D | 5 | 0 $Ca^{+2}$ | 10,000 PBTC | 28.8% |
| 2E | 0 | 0 $Ca^{+2}$ | 10,00 EDTA | 0% |
| 2F | 5 | 500 $Ca^{+2}$ | 0 EDTA | 10.7% |
| 2G | 5 | 500 $Ca^{+2}$ | 10,000 PBTC | 25.9% |
| 2H | 5 | 0 $Ca^{+2}$ | 10,000 PBTC | 26.3% |

TABLE 3

| Sample # | Dosage of Anionic Polymer (ppm) | Hardness Dosage (ppm) | Chelant (ppm) | % Relative Fluorescence Change (PRFC) |
|---|---|---|---|---|
| 3A | 0 | 0 $Mg^{+2}$ | 10,000 PBTC | 0% |
| 3B | 5 | 500 $Mg^{+2}$ | 0 PBTC | 12.3% |
| 3C | 5 | 500 $Mg^{+2}$ | 10,000 PBTC | 26.6% |
| 3D | 5 | 0 $Mg^{+2}$ | 10,000 PBTC | 27.8% |

EXAMPLE 4

The linearity of % Relative Fluorescence Change versus anionic polymer concentration was measured. The anionic polymer was added first and concentration is listed as actives equivalent in 1 mL volume (column 1 of Table 4). Next, chelant (neutralized to pH 7 with sodium hydroxide) was added in concentration at an actives equivalent of 10,000 ppm in 1 mL volume. Next, $Ca^{+2}$ hardness was added as calcium chloride at 200 ppm $Ca^{+2}$ (as $CaCO_3$) equivalent in 1 mL volume. Next, magnesium hardness was added as magnesium sulfate at 200 ppm $Mg^{+2}$ (as $CaCO_3$) equivalent in 1 mL volume. Next, bicarbonate alkalinity was added at 200 ppm dosage (as $CaCO_3$) equivalent in 1 mL volume. Sample volume was diluted to 8 mL; then 2 mL Nile Blue A (0.0619 g/mL) was added and % Relative Fluorescence Change (excitation@670 nm and emission @690 nm) was taken after 3 minutes. The results are summarized in Table 4. The coefficient of linear correlation (r) is 0.994, where r=1.000 is perfect linearity.

TABLE 4

| Dosage of Anionic Polymer (ppm) | % Relative Fluorescence Change (PRFC) |
|---|---|
| 0.0 | 0.0% |
| 1.0 | 2.6% |
| 2.0 | 3.9% |
| 3.0 | 5.5% |
| 4.0 | 8.8% |
| 5.0 | 10.0% |
| 7.5 | 16.0% |
| 10.0 | 24.0% |

EXAMPLE 5

Figure 3:
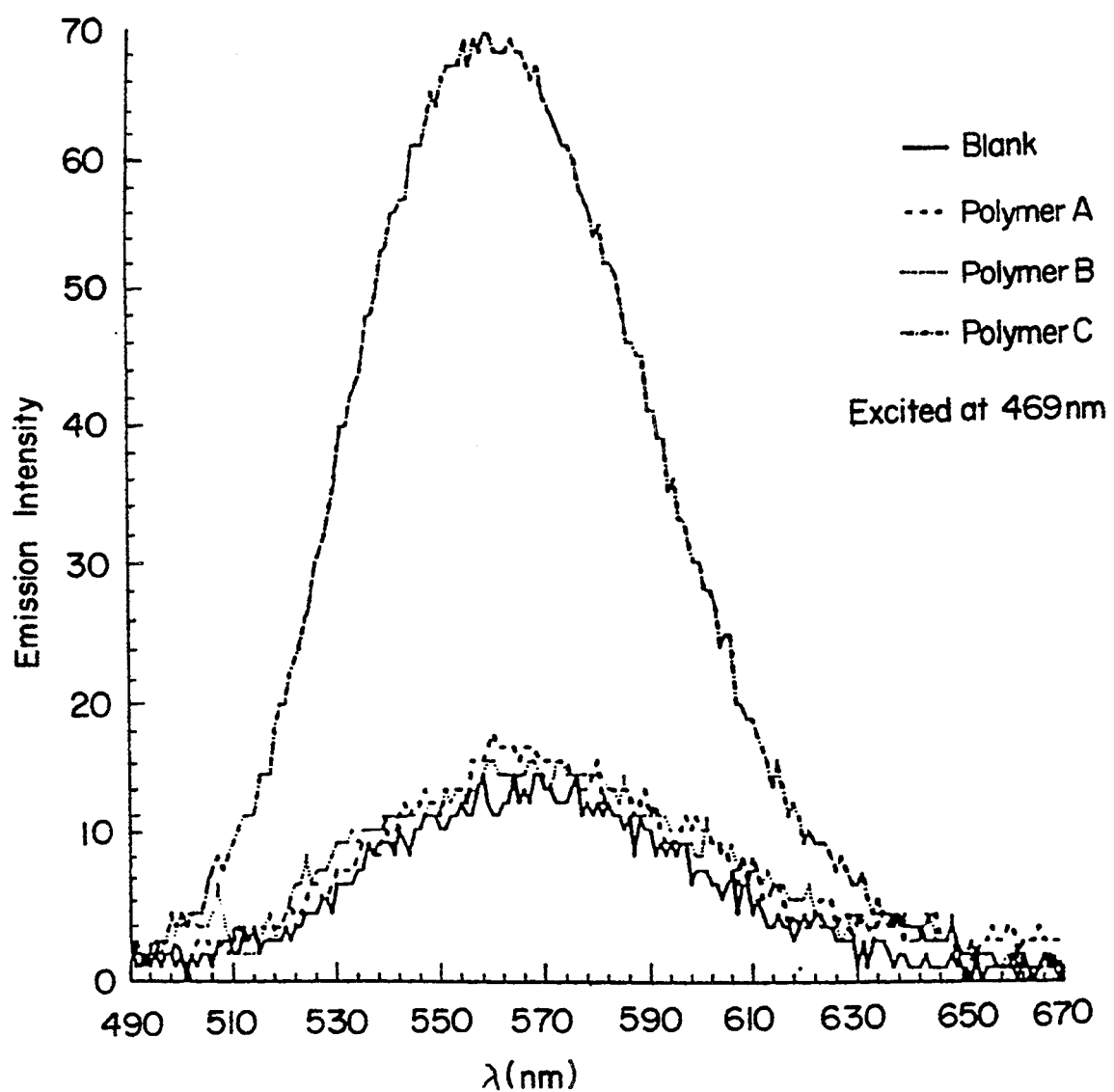
FIG. 3 is a plot showing the fluorescence spectrums of aqueous solutions of a cationic fluorochromatic reagent in the absence and presence of anionic polymers at a pH of about 5.

The fluorescence intensity of 2-(4-(dimethylamino)-styryl)-1-methylpyridinium iodide (FW of 366.25 and absorption maximum at 466 nm), a cationic fluorescent reagent, has been found to increase at its normal peak emission wavelength in the presence of polymethacrylic acid in aqueous solution. The increase in fluorescence intensity was about 45 percent when the solution pH was about 5, and shown in FIG. 3, which is plot of emission intensity versus wavelength (emission spectrum) for a blank (dye alone), and for the fluorescent reagent in the presence of Polymer A (the polymethacrylic acid), Polymer B and Polymer C, which were not polymethacrylic acid polymers. The spectrums are differentiated by line type and labeled by the identity of the polymer. The spectrums each extend through the wavelength range of from 500 to 640 nm.

TABLE 5

| Dosage of Anionic Polymer (ppm) | % Relative Fluorescence Change (PRFC) |
|---|---|
| 0.0 | 0.0% |
| 2.5 | 2.0% |
| 5.0 | 6.0% |
| 10.0 | 16.0% |

As used herein "water treatment agent", "treatment agent" and "active water treatment agent, all interchangeable alternative terminology, mean an active treatment agent or "actives" as the term "actives" is used in the technical field. In contrast, a water treatment feed and/or product may contain a plurality of treatment agents and/or diluents therefor and/or other substances that are not water treatment agents. Likewise the term "polyelectrolyte" as used herein means polymer actives, while a polyelectrolyte feed or product may contain components in addition to the polyelectrolyte.

As used herein, system consumption is a selective change in the concentration of a substance in an aqueous system being treated, and is commonly but not necessarily a loss of the substance from a system. The selective loss of substance, such as polyelectrolyte due to precipitation would be the system consumption for the polyelectrolyte. The system consumption being measured by the present invention, to the extent that a plurality of system consumption factors are acting on the polyelectrolyte in-system concentration, is a net system consumption, relative of course to the in-system concentration of the associated inert tracer. The term "in-system concentration" in all instances refers to the concentration of a specie(s) within the water of a water system, to the exclusion of any amount of such specie(s) not dispersed within the water, regardless of whether such excluded amount is in contact with such water, for instance as a deposit formed on a surface in contact with such water.

The industrial water systems for which the present invention may be used are water systems of any industry which employs at least one polyelectrolyte, including without limitation temperature conditioning water systems (wherein the waters are being used as a heat-/energy transfer media), water systems wherein a raw water stream and/or water for makeup use is being purified, a water system wherein waste materials and/or waste waters are being purified, a water system wherein solids (suspended and/or solutes) are being separated from liquids (for instance the water system of membrane-separation processes), water systems of manufacturing processes, particularly chemical industry manufacturing processes, including without limitation the processes of the pulping and papermaking industries, the steel industry, the metal working industries, the food processing industries, the mining industries, the automotive industry, the textile industry, utilities, chemical processing industries, manufacturing industries, spray paint industries, refining industries such as the refining of aluminate, and the like.

Industrial water system often are fluid systems that contain at least about 60 weight percent water, the remainder being solids (suspended and/or dissolved) and/or nonaqueous fluids, and which commonly are flowing rather than static. In preferred embodiment the industrial water system of the present invention is an industrial system that contains at least about 65 or 70 weight percent water, the remainder being solids (suspended and/or dissolved) and/or nonaqueous fluids, and preferably which is flowing rather than static.

The present invention in broad embodiment, however, is not limited to industrial water systems, and instead may be applicable to nonaqueous fluid systems. There might be instances of the use of polyelectrolyte in substantially nonaqueous fluid systems, for instance in some hydrocarbon streams in the oil refining industry. It may be highly beneficial to monitor the concentration of polyelectrolyte in such hydrocarbon streams for the purpose of the present invention. The process of the present invention may be employed for mixed aqueous/nonaqueous fluid systems and nonaqueous fluid systems in the same manner as in aqueous systems, provided any potential interference with the fluorochromatic interaction and/or the fluorescence analysis arising from the nonaqueous portion of the fluid can be avoided. Since the present invention is believed to be most readily and commonly adaptable to water systems, for simplicity but not for limitation purposes the invention is described herein in terms of water systems.

Unless expressly indicated otherwise herein, the inclusion of a prefix or suffix in parenthesis designates the word with such prefix or suffix as an alternative. For instance, "active(s)" means "active and/or actives," "(meth)acrylamide" means "acrylamide and/or methacrylamide", "specie(s)" means "specie and/or species", "determination(s)" means "determination and/or determinations", "technique(s)" means "technique and/or techniques", "location(s)" means, "chemical(s)" means "chemical and/or chemicals", "component(s)" means "component and/or components", "tracer(s)" means "tracer and/or tracers", and the like. By "ppm" is meant "parts per million" by weight. By "ppb" is meant "parts per billion" by weight. By "ppt" is meant "parts per trillion" by weight.

We claim:

1. A method for monitoring and/or controlling the concentration of a polyelectrolyte in the water of an aqueous system comprising:

withdrawing a sample of said water;

adding a known or standard amount of a fluorochromatic reagent to said sample;

directing light energy of a selected excitation wavelength for said fluorochromatic reagent into said sample whereby light energy is available for absorption by said fluorochromatic reagent;

measuring the intensity of light emitted about a selected fluorescence emission wavelength for said fluorochromatic reagent;

comparing said intensity of said emitted light to a standard curve, said standard curve comprising a plot of fluorescence emission intensity of said fluorochromatic reagent in the presence of a polyelectrolyte versus concentration said polyelectrolyte; and determining from said comparison the concentration of a polyelectrolyte in said sample of water.

2. The process of claim 1 wherein said standard curve contains a correction for background fluorescence normal to said aqueous system.

3. The process of claim 1 wherein said standard curve is calibrated on the basis of concentration of polyelectrolyte ionic sites and the measure of said polyelectrolyte concentration is said concentration of polyelectrolyte ionic sites.

4. The process of claim 1 wherein said fluorochromatic reagent is one that provides one fluorochromatic behavior selected from the group consisting of an increase in the fluorescent emission intensity at said selected emission in the presence of the polyelectrolyte and a decrease in the fluorescent emission intensity at said selected emission in the presence of the polyelectrolyte.

5. The process of claim 1 wherein the target in-system concentration of said polyelectrolyte in said aqueous system is from about 0.1 ppm to about 200 ppm, based on parts by weight of said polyelectrolyte per million parts by weight of said water of said aqueous system.

6. The process of claim 1 wherein said fluorochromatic measurement of said concentration of polyelectrolyte at least determines that transport of said polyelectrolyte to the site at which said sample was taken has occurred.

7. The process of claim 1 wherein said fluorochromatic measurement of said concentration of polyelectrolyte determines an underfeeding or overfeeding of said polyelectrolyte, and provides a signal that activates and/or regulates the feed of said polyelectrolyte to said aqueous system.

8. The process of claim 1 wherein said fluorochromatic reagent is Nile Blue A.

9. The process of claim 1 wherein said fluorochromatic reagent is pinacyanol chloride.

10. The process of claim 1 wherein said fluorochromatic reagent is 2-(4-(dimethylamino)styryl)-1-methylpyridinium iodide.

11. The process of claim 1 wherein said polyelectrolyte is a polymeric scale inhibitor, corrosion inhibitor and/or dispersant within the weight average molecular weight range of from about 500 to about 300,000, and has an anionic charge density of at least about 10 mole percent based on mer units containing at least one anionic site, said mer units being a segment of said polyelectrolyte containing two backbone carbons.

12. The process of claim 1 wherein said fluorochromatic measurement of said concentration of polyelectrolyte determines an underfeeding or overfeeding of a plurality of water treatment agents.

13. The process of claim 1 wherein an inert tracer is added to said aqueous system in known proportion to the said polyelectrolyte, and wherein the concentration of said inert tracer in said aqueous system at a site remote from said addition site and at a time after the addition time is determined by an analytical technique effective for said inert tracer in said aqueous system, wherein the concentration of the polyelectrolyte is calculated from the determined concentration of the inert tracer.

14. The process of claim 3 wherein a system consumption value for said polyelectrolyte is determined by subtracting the concentration of the polyelectrolyte as determined by the measurement of the inert tracer from the concentration of polyelectrolyte as determined from the standard curve based on use of fluorochromatic reagent, wherein, said system consumption is the amount of polyelectrolyte selectively consumed per unit volume of water of said aqueous system.

15. The process of claim 4 wherein the in-system concentration of said polyelectrolyte in said aqueous system is adjusted to provide a substantially optimal in-system concentration based on said system consumption.

16. The process of claim 3 said inert tracer is added to said aqueous system at a in-system concentration at least sufficient to provide a concentration of tracer in said sample of at least about 0.1 ppb, and
wherein said inert tracer is at least one compound selected from the group consisting of the monosulfonated, disulfonated and trisulfonated naphthalenes isomers, and the sulfonated derivatives of pyrene and the water-soluble salts thereof, and said concentration of said inert tracer is determined by fluorescence analysis.

17. The process of claim 12 wherein said determination of said concentration of said polyelectrolyte is made on a substantially continuous basis.

18. A method for monitoring and/or controlling the concentration of a polyelectrolyte in the water of an industrial aqueous system comprising:
withdrawing at least one sample of water from said industrial aqueous system;
adding a known amount of a fluorochromatic reagent to said sample;
directing light energy of a selected excitation wavelength for said fluorochromatic reagent into said sample, whereby the light energy is available for absorption by said fluorochromatic reagent;
measuring the intensity of light emitted about a selected fluorescence emission wavelength for said fluorochromatic reagent;
then comparing said intensity of said emitted light to a standard curve, said standard curve comprising a plot of fluorescence emission intensity of said fluorochromatic reagent in the presence of a polyelectrolyte versus concentration said polyelectrolyte;
determining from said comparison the concentration of said polyelectrolyte in said sample of water;
adding an inert tracer to said industrial aqueous system in known proportion to the said polyelectrolyte, and
determining the concentration of said inert tracer in said aqueous system by an analytical technique effective for said inert tracer in said aqueous system.

19. A method for monitoring and/or controlling the concentration of a polyelectrolyte in the water of an industrial aqueous system comprising:
withdrawing at least one sample of water from said industrial aqueous system;
adding a known amount of a fluorochromatic reagent to said sample;
directing light energy of a selected excitation wavelength for said fluorochromatic reagent into said sample, whereby the light energy is available for absorption by said fluorochromatic reagent;
measuring the intensity of light emitted about a selected fluorescence emission wavelength for said fluorochromatic reagent;
then comparing said intensity of said emitted light to a standard curve, said standard curve comprising a plot of fluorescence emission intensity of said fluorochromatic reagent in the presence of a polyelectrolyte versus concentration said polyelectrolyte; and determining from said comparison the concentration of said polyelectrolyte in said sample of water;

wherein said determination of said concentration of said polyelectrolyte is made on a substantially continuous basis.

20. The method of claim 19 wherein an inert tracer is added to said industrial aqueous system in known proportion to the said polyelectrolyte, and further including determining the concentration of said inert tracer in said aqueous system by an analytical technique effective for said inert tracer in said aqueous system.

* * * * *

UNITED STATES PATENT AND TRADEMARK OFFICE
CERTIFICATE OF CORRECTION

PATENT NO. : 5,389,548
DATED : February 14, 1995
INVENTOR(S) : John E. Hoots, et al It is certified that error appears in the above-indentified patent and that said Letters Patent is hereby corrected as shown below:

Column 33, Line 60, Claim 14

14. The process of claim 3 wherein a system con-

SHOULD READ

14. The process of claim 13 wherein a system con-

Column 34, Line 1, Claim 15

15. The process of claim 4 wherein the in-system

SHOULD READ

15. The process of claim 14 wherein the in-system

UNITED STATES PATENT AND TRADEMARK OFFICE
CERTIFICATE OF CORRECTION

PATENT NO. : 5,389,548
DATED : February 14, 1995
INVENTOR(S) : John E. Hoots, et al It is certified that error appears in the above-indentified patent and that said Letters Patent is hereby corrected as shown below:

Column 34, line 6, Claim 16
"16. The process of claim 3 said inert tracer is added to" should read
--16. The process of claim 13 said inert tracer is added to--

Signed and Sealed this

Fourth Day of April, 1995

Attest:

BRUCE LEHMAN

Attesting Officer

Commissioner of Patents and Trademarks